(12) United States Patent
Chen

(10) Patent No.: US 6,180,344 B1
(45) Date of Patent: Jan. 30, 2001

(54) 5' UPSTREAM REGION SEQUENCES OF THE MYOD1 GENE AND USES THEREOF

(76) Inventor: Bin Chen, #4 Glen Valley Ct., Little Rock, AR (US) 72223

( * ) Notice: Under 35 U.S.C. 154(b), the term of this patent shall be extended for 0 days.

(21) Appl. No.: 09/193,792

(22) Filed: Nov. 17, 1998

Related U.S. Application Data

(60) Provisional application No. 60/065,113, filed on Nov. 18, 1997, now abandoned.

(51) Int. Cl.$^7$ ....................................... C12Q 1/68
(52) U.S. Cl. ........................... 435/6; 435/91.1; 435/91.2; 435/456; 435/4; 435/320.1
(58) Field of Search ................................ 435/6, 91.1, 91.2, 435/456, 4, 320.1, 325; 536/24.3, 24.31, 24.33, 23.1, 23.4

(56) References Cited

U.S. PATENT DOCUMENTS 5,843,649 * 12/1998 Stoerker et al. ..................... 435/6
5,922,601 * 7/1999 Baetscher et al. ................... 435/456

* cited by examiner

*Primary Examiner*—W. Gary Jones
*Assistant Examiner*—Janell E. Taylor
(74) *Attorney, Agent, or Firm*—Benjamin Aaron Adler

(57) ABSTRACT

MyoD1 expression is found at early stages of embryonic myogenesis and in rhabdomyosarcoma, the most common soft-tissue cancer in children. Hypomethylation of a CpG island in the 5' upstream region of the human MyoD1 gene occurs in a majority of alveolar rhabdomyosarcomas, and may be responsible for higher levels of the MyoD1 expression in this tumor type. The methylation status of the upstream CpG island may play a key role in regulation of the MyoD1 expression not only in alveolar rhabdomyosarcoma, but also during normal development. This invention provides for the assessment of the methylation status of the MyoD1 upstream CpG sites, which may have valuable implications for differential diagnosis of pediatric cancers and may results in potential therapeutic applications.

20 Claims, 15 Drawing Sheets

```
-1537  AGGAAGAGAGGC TGAGAGACCC CCATGGGGGT GGCCGGTATG CTGAGGCTTG TATGGGAGCC  -1478
                                          MspI/HpaII

-1477  AGATATCCCA CATCCCATGG GGTGGTTGCC TCCTCCTGTT TCCAGCCTTT CCAGTGAGGC  -1418
-1417  TGCAGGAAAG AGACACAGCT AAGGCCTGGA GACTCGTGGC ACTCCGTGAG GGCATGGTAC  -1358
       PEA3                                         CRE
       PstI

-1357  CACAGATGAG TTGTAAGCCT GCGGGACACA GCATCCAACT CTGAAAGCCC CTTGCTCGAA  -1298
       bHLH

-1297  TAACCCTACA TCACCGCCTG AGGGCTTCCA TATCCTTGGT CTCTTCAGAC TGTCATCCCC  -1238
-1237  ACCACAATTA CTCCAAGAAA TTACTGTCAT CCCCAAATCT ATAACTGGAA ACTGAGGCTC  -1178
-1177  AGGAAGGAGA CATGACTTCC ACAAAATCAC ACAGTTGGGA AACTCTGGAG TCTGCACTCA  -1118
       PEA3                             bHLH

-1117  ACTGGTCTGC AAACCGACTC TCGGAGACTT CAGGTGAGAT GAGGTCAGGT TCTCAGGCCA  -1058
       bHLH                             bHLH

-1057  GGTCCTGAAG TTTGACACCT TGGCGAAATG CACTTTCCTT GACTCAGCAC CGCAGTGACG  -998
                                                  AP1

-997   GCGGAACGAA GCCCCGAGCA GAAGGGCTTT TCTTCCCAGC TGAAGAGGCA GCTCAGCCTA  -938
-937   GACCCCAGGC ATGGCACTGG ACACCCCTGC TGTGGAAACG TGCAGATTTA GATGGAGGGG  -878
       AP2                                                  bHLH
                                       AP3

-877   ATTCCTAACC TGGGCAGGAT CCGAGTTTGG AGAGATTGGC GCGAAGTTTA GCAGCAATCT  -818
                       BamHI                                HhaI

-817   CCGATTCCTG TACAACCATA GCTGGGTTTC TAAGCGTCTA GGGAAGAAGG ACTGGGCCCA  -758
-757   CGACCTGCTG AGCAACTCCC AGTCGGGGA CTGGCGGAAT ATCAGAGCCT CTACGACCCG  -698
-697   TTTGTCTCGG GCTCGCCCAC TTCAACTCTC GGGGTCTCTC CGCCTGTTGT TGCACTCGTG  -638
```

FIG. 2-1

```
-637   CGTTCTCTGC CCCTGACGCT CTAAGCTTTC TGCTTTCTGC GTGTCTCTCA GCCTCTTTCG  -578
-577   GTCCCTCTTT CACGGTCTCA CTCCTCAGCT CGTGCCCCCC AATGCCTTGC CTCTCTCCAA  -518
       Pax3

-517   ATCTCTCACG ACCTGATTTC TACAGCCGCT CTACCCATGG GTCCCCCACA AATCAGGGGT  -458
                                              AP2

-457   ACAGAGGAGT ATTGAAAGTC AGCTCAGAGG TGAGCGCGCG CAGCCAGCGT TTCCCGCGGA  -398
                                            HhaI

-397   TACAGCAGTC GGGTGTTGGA GAGGTTTGGA AAGGGCGTGC CGGAGAGCCA AGTGTCAGCC  -338
                                                                  bHLH
                                                       MspI/HpaII

-337   GCCTAGGGCT TGCCGGTCGC TCCCTCCCTC CCTGCCCGGT AGGGGACCTA GCGCGCACGC  -278
-277   CAGTGTGGAG GGGCGGGGCTG CTCGGGCCCC CTCGGGCCAGT TCGGCCACCC CGGGGACCCC  -218
                Sp1                 AP2                          AP2  AP2
                                                                   SmaI

-217   CCCCAAGCCC CGCCCCCCGAG TGTTCCTATT GGCCCTCGGAC TCCCCCCTCCC CCAGCTGCCC  -158
       ------------ AP2                  CAAT_REV                  AP2  --------
                                                                        bHLH

-157   GCCTGGGCTC CGGGGGCGTTT AGGCTACTAC GGATAAATAG CCCAGGGCGC CTGGCCCGAGA   -98
                              PEA3                   TATA         AP2   EheI

-97   AGCTAGGGGT GAGGAAGCCC TGGGGCGCTG CCGCCGCTTT CCTTAACCAC AAATCAGGCC   -38
                                                                    1

-37   GGACAGGAGA GGGAGGGGTG GGGGACAGTG GGTGGGatt cagactgcca gcactttgct  +23

+24   atctacagcc ggggctcccg agcggcagaa agttccggcc actcctgcc gcttgggttg  +83

+84   ggcgaaagcc aggaccgtgc cgcgccaccgc caggatatgg agctactgt cgccaccgct  +143
+144   ccggacgta gacctgacgg ccccccgacgg ctctcctgc tcctttgcca caacggacga  +203
```

FIG. 2-2

```
+204  cttctatgac gacccgtgtt tcgactcccc ggacctgcgc ttcttcgaag acctgaccc  +263
+264  gcgcctgatg cacgtgggcg cgctcctgaa acccgaagag cactcgcact tccccgcggc  +323
+324  ggtgcacccg gccccgggcg cacgtgagga cgagcatgtg cgccgcgccc gcgggcacca  +383
             SmaI +384  ccaggcgggc cgctgcctac tgtgggcctg caaggcgtgc aagcgcaaga ccaccaacgc  +443
+444  cgaccgccgc aaggcccgcca ccatgcgcga gcgcgccgc ctgagcaaaag taaatgaggc  +503
+504  ctttgagaca ctcaagcgct gcacgtgcag caatccaaac cagcggttgc ccaaggtgga  +563
+564  gatcctgcgc aacgccatcc gctatatcga gggcctgcag gctctgctgc gcgaccagga  +623
                                          PstI +624  cgccgcgccc cctggcgcag ccgccttcta tgcgccgggc ccgctgcccc cgggccgcgg  +683
+684  cggcgagcac tacagcggcg actccgacgc gtccagcccg cgctccaact gctccgacgg  +743
+744  catg (SEQ ID NO. 1)
```

FIG. 2-3

5' UPSTREAM REGION SEQUENCES OF THE MYOD1 GENE AND USES THEREOF

CROSS-REFERENCE TO RELATED APPLICATION

This patent application claims benefit of provisional patent application U.S. Ser. No. 60/065,113, filed Nov. 18, 1997, now abandoned.

BACKGROUND OF THE INVENTION

1. Field of the Invention

The present invention relates generally to the field of molecular biology and muscle physiology. More specifically, this invention relates to the MyoD1 gene, the methylation pattern within the 5' upstream region of this gene, and diagnostic and therapeutic applications thereof.

2. Description of the Related Art

Rhabdomyosarcoma is the most common soft-tissue malignancy in childhood, accounting for 4 to 8% of all pediatric cancers (Enzinger and Weiss, 1995). Rhabdomyosarcomas are a heterogeneous group of malignancies characterized by varying degrees of differentiation, ranging from uncommitted primitive mesenchymal cells to fetal myotubes (Parham, 1995). Because of the clinical heterogeneity and the primitive histologies, it is often a challenging task to diagnose poorly differentiated rhabdomyosarcomas from other small round cell tumors.

Within the class of pediatric rhabdomyosarcomas, there are two major subtypes, embryonal and alveolar, which present with biologically and clinically distinct behaviors. The botryoid and the spindle cell variants of embryonal rhabdomyosarcoma are associated with favorable prognosis (Leuschner et al, 1993), whereas alveolar rhabdomyosarcomas usually have a more aggressive clinical behavior and are associated with a worse outcome than all embryonal variants (Tsokos et al, 1985). The molecular events that are involved in the development of a rhabdomyosarcoma are still poorly understood. The discovery of the MyoD gene family, however, has provided insight into the regulation of myogenesis and has prompted the search for applicable markers that can assist in the clinical diagnosis of rhabdomyosarcomas (Weintraub et al, 1991).

The genes of the MyoD family create the nodal point of early myogenesis by upregulating the expression of myogenic genes such as desmin, creatine kinase, and myosin (Weintraub et al, 1991). Members of the MyoD family, including MyoD1, myogenin, myf-5, and myf-6, are characterized by a helix-loop-helix motif with an adjacent basic domain (bHLH), and are part of a large class of transcription activators (Braun et al, 1989; Davis et al, 1987; Rhodes, 1989; Wright et al, 1989). Arbitrary expression of these genes causes initiation of myogenesis not only in primitive mesenchymal cells but also in differentiated non-muscle cells such as fibroblasts (Weintraub et al, 1991).

Among these genes, the MyoD1 has been the most studied in rhabdomyosarcoma. The MyoD1 gene product functions as a homodimer or heterodimer by binding to the protein product of the E2A gene, causing transcription activation (Davis et al, 1990), or to the Id protein, causing transcription inhibition (Li and Olsen, 1992). In normal myogenesis, as occurs in growth and repair, the expression of MyoD1 initiates a cascade of events leading to the formation of a myotube, and is subsequently suppressed (Montarras et al, 1991; Ott et al, 1991). In rhabdomyosarcoma, the molecular events that cause the inhibition of MyoD1 expression are distorted or lost, so that the expression of MyoD1 persists at high levels in tumor cells (Tapscott et al, 1993). As a result, the MyoD1 protein has been recognized as a sensitive and specific marker for both childhood and adult rhabdomyosarcomas.

Abnormal patterns of DNA methylation are thought to play an important role in the development of cancer by altering gene expression and causing genomic instability (Bird, 1996). De novo methylation of the human MyoD1 gene has been observed in a number of neoplasms, including colorectal cancer (Iacopetta et al, 1997), breast carcinomas (Hahnel et al, 1996), and ovarian carcinomas (Cheng et al, 1997). In those studies, however, the tumors were of non-muscle origins where the MyoD1 gene is not expressed due to unknown silencing mechanisms. Therefore, the relationship between hypermethylation of certain MyoD1 regions and tumor development was unclear. In addition, a mouse or a human MyoD1 cDNA probe was used that would only allow detection of methylation alterations in the coding region but not the 5' upstream region where the transcriptional promoter is usually located.

MyoD1 has been implicated in the control of proliferation in both normal cells and tumors, independent of its role in the activation of the myogenic differentiation program (Crescenzi et al, 1990, Sorrentino et al, 1990). De novo methylation of the murine MyoD1 upstream CpG island occurs during the establishment of immortal cell lines (Jones et al, 1990), and progressive increases in the methylation status and heterochromatization of the CpG island was found during oncogenic transformation (Rideout et al, 1994). However, these two findings are thought to be in vitro phenomena related to cell culturing situations, because the mouse MyoD1 gene was found unmethylated in skeletal muscle and non-muscle cells which do not express the gene. Of interest has been the observation that patchy, heterogeneous expression of MyoD1 is frequently observed in embryonal rhabdomyosarcoma, whereas strong diffuse positivity is usually observed in alveolar rhabdomyosarcomas. This phenomenon was also reflected by Northern blot analysis in a study by Scrable et al. which indicated that higher levels of MyoD1 mRNA transcripts are produced in alveolar rhabdomyosarcomas as compared to tumors of the embryonal subtype (Scrable et al., 1989).

The human MyoD1 gene is mapped to chromosome 11p15.4 (Scrable et al., 1990), adjacent to a number of imprinted genes including IGF2, H19, and $p_{57}^{KIP}$, all of which have shown imprinting disturbances leading to aberrant gene expression associated with abnormal development and cancer (Ogawa et al., 1993; Taniguchi et al., 1997; Taniguchi et al., 1995). Loss of heterozygosity for chromosome 11p15, together with loss of imprinting for genes in this region, is found frequently in embryonal rhabdomyosarcomas (Ohlsson et al., 1993; Scrable et al., 1989). Overexpression of the MyoD1 and IGF2 are both found in the embryonal subtype of rhabdomyosarcoma, which occurs with a n increased incidence in Beckwith-Wiedemann syndrome (Dias et al, 1990; Ohlsson et al, 1993; Sotelo-Avila and Gooch, 1976). On the other hand, hypermethylation at CpG islands of tumor suppressor genes is known to silence their expression in tumorigenesis, as demonstrated for the VHL gene in renal tumors (Herman et al., 1994) and the $p16^{INK4A}$ in a variety of malignancies (Ng et al., 1997).

Alveolar rhabdomyosarcomas, on the other hand, are characterized by chromosomal translocations t(2;13) or t(1;13), which respectively generate the Pax3-FKHR or the Pax7-FKHR fusion genes (Barr et al., 1993; Davis et al., 1994). Two recent studies on mouse skeletal myogenesis suggested that Pax3, an evolutionarily conserved transcription factor expressed in the lateral dermomyotome, may control myogenesis either by directly activating the transcription of the MyoD1 gene (Tajbakhsh et al, 1997), or by mediating the transcriptional activation of MyoD1 and Myf-5 in response to muscle-inducing signals (Maroto et al, 1997). In humans, a chromosomal translocation t(2;13) juxtaposes the amino terminal DNA binding domains of PAX3 with the transcriptional activation domain of FKHR (a Forkhead family member) in alveolar rhabdomyosarcoma (Galili et al. 1993). The tumor-specific Pax3-FKHR fusion protein is a more potent transcription activator than the wild-type Pax3 protein (Sublett et al, 1995), suggesting that a gain-of-function of Pax3 may therefore be involved in the etiology of alveolar rhabdomyosarcoma. This argument is further strengthened by the identification of a less frequent translocation t(1;13) in alveolar rhabdomyosarcoma which rearranges PAX7, another member of the Pax family, to generate a Pax7-FKHR chimera, analogous to the Pax3-FKHR fusion (Davis et al, 1994). Therefore, it appears that there is a relationship between the high level of MyoD1 expression and the characteristic Pax3-FKHR or Pax7-FKHR fusion products in alveolar rhabdomyosarcoma.

The identification of a potential Pax3 consensus binding site in the promoter region of the MyoD1 gene (−578 through −569) suggests that Pax3 may activate the MyoD1 transcription by directly binding to the MyoD1 promoter. A similar Pax3 binding site has been identified in the promoter region of the c-Met proto-oncogene, which is expressed in limb muscle progenitors and is required in the mouse for the limb muscle development (Epstein et al, 1996). Pax3 binding site in the c-Met promoter may contribute to direct transcription regulation by Pax3 (Epstein et al, 1996). However, unlike MyoD1 expression, which is found in most rhabdomyosarcomas and establishes the diagnosis of this tumor type, c-Met expression is less consistently found in rhabdomyosarcoma cell lines, and is unlikely to account for the Pax3-FKHR or Pax7-FKHR tumorigenicity. In addition, the Pax3-FKHR or Pax7-FKHR fusion proteins in alveolar rhabdomyosarcoma have been shown to bind similar nuclear DNA targets but are more potent transcription activators than the wild-type Pax3 or Pax7 (Sublett et al, 1995). Therefore, the Pax3-FKHR or Pax7-FKHR fusion proteins might be responsible in part for the enhanced transcription activation of the MyoD1 gene in alveolar rhabdomyosarcoma, presumably by binding to the Pax3 consensus site in the promoter region of the MyoD1 gene.

The MyoD1 gene consists of three exons, and is highly conserved in mammalian species. The mouse MyoD1 gene has a relatively large CpG island that spans the first exon and extends a short distance both 5' and 3' from the first exon (Rideout et al, 1994). In mouse, methylation has been shown to play a role in preventing MyoD1 expression in cultured non-muscle cells. Demethylation of the MyoD1 gene initiates the myogenic program in murine fibroblasts (Konieczny and Emerson, 1984), whereas methylation of the MyoD1 promoter region may turn off MyoD1 expression both in myoblasts and in fibroblasts (Zingg et al, 1991). However, a correlation between the MyoD1 gene methylation status and its level of expression has not been demonstrated. The human MyoD1 mRNA was cloned in 1991 (Pearson-White, 1991).

Thus, the prior art is deficient in the understanding of how the MyoD1 gene is regulated during normal myogenesis and rhabdomyosarcoma and the effect methylation of the MyoD1 gene has on gene expression. The prior art is also deficient in the ability to accurately diagnose rhabdomyosarcoma from other small round cell pediatric tumors and to differentiate the alveolar subtype of rhabdomyosarcoma from the embryonal subtype. The present invention fulfills these long-standing needs and desires in the art.

SUMMARY OF THE INVENTION

The molecular events that determine the temporal and spatial expression of the MyoD1 gene are complex and many key elements remain to be elucidated. Though sharing the common feature of expressing the MyoD1 gene, embryonal and alveolar rhabdomyosarcomas have distinct etiologies. In contrast to alveolar rhabdomyosarcomas in which the 5' flanking region of the MyoD1 gene is unmethylated, embryonal rhabdomyosarcomas show a partial methylation pattern of this region which is present in normal fetal muscle cells but not in differentiated muscle or non-muscle cells. This indicates that embryonal rhabdomyosarcomas resemble normal fetal muscle, not only in histology but also at the molecular level, with regard to the promoter methylation and expression pattern of the MyoD1 gene. Higher levels of MyoD1 expression is found in alveolar rhabdomyosarcomas in relation to the embryonal subtype, again consistent with the presence of an unmethylated MyoD1 promoter in the alveolar tumors. The distinct MyoD1 methylation patterns in the two major subtypes of rhabdomyosarcoma are consistent with their divergent levels of MyoD1 expression, and are therefore diagnostic.

Thus, the present invention discloses the sequence of the upstream region of the human MyoD1 gene, which contains the transcriptional promoter. The MyoD1 5' region, and the probes resulting thereof, may be used to determine the methylation state of the MyoD1 promoter in a patient suspected of having rhabdomyosarcoma or other soft-tissue tumors. One object of the present invention is to provide a method of diagnostic evaluation based on the methylation state of the MyoD1 promoter.

In an embodiment of the present invention, there is provided an isolated DNA molecule encoding the promoter region of MyoD1 having the sequence shown in SEQ ID No. 1.

In another embodiment of the present invention, there is provided isolated DNA molecules, useful as, e.g., probes comprising subsets of the MyoD1 promoter region described in SEQ ID No. 1. These probes are designated PP2.0, PB0.5, and SS0.5 (SEQ ID No. 2, SEQ ID No. 3, and SEQ ID No. 4, respectively).

In yet another embodiment of the present invention, there is provided a method by which the methylation status of the promoter region of the MyoD1 gene can be assessed in an individual in need of such an assessment, wherein the methylation status of the MyoD1 promoter region can be used as a diagnostic tool for rhabdomyosarcoma or other soft-tissue cancers.

Other and further aspects, features, and advantages of the present invention will be apparent from the following description of the presently preferred embodiments of the invention. These embodiments are given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIG. 2 shows the nucleotide sequence of the promoter region of the human MyoD1 gene (SEQ ID No. 1). The potential transcriptional elements are underlined. Base numbering is relative to the start site of the cDNA sequence. The BamHI restriction site at −861, the HhaI sites at −839 and −424, the MspI/HpaII sites at −1505 and −358, the PstI site at −1418, the EheI site at −102, and the SmaI site at −229 are indicated.

FIG. 3 shows the methylation of the MyoD1 upstream region in normal tissues.

FIG. 4 shows the hypomethylation of the MyoD1 upstream region in 3 alveolar rhabdomyosarcomas.

FIG. 7 shows the hypomethylation and partial deletion of the MyoD1 5' region in an embryonal rhabdomyosarcoma.

FIG. 11A shows a schematic map of this region. FIG. 11B shows Southern blot analysis. DNA samples from 50 day-, 100 day-, 22 week-, 27 week, and 36 week-old fetuses were digested with MspI (M), HpaII (Hh), HhaI/HpaII, and HhaI (Hh), electrophoresed in 1% agarose gel, blotted, and hybridized to probe PB0.5 (filled rectangle). Methylation at HhaI sites B and C results in the 4.8 kb HhaI A–D fragment, whereas methylation at HhaI site B only led to the 4.4 kb HhaI A–C. The 1.1 kb HpaIIC-HhaID fragment in 100 day-, 22 week-, and week-old fetuses is a result of progressive methylation of HhaI-site C.

FIG. 12A shows a schematic map. FIG. 12B shows the Southern blots. DNA was digested with MspI (M), HpaII (Hh), and HhaI (Hh), electrophoresed in 1% agarose gel, blotted, and hybridized to MyoD1 enhancer probe (filled rectangle). The HpaII 1–6 fragment results from methylation at HpaII sites 2–5. The 7.4-kb HpaII 4–6 fragment is present only in the tumors and is a result of demethylation at HpaII site 4. Upon HhaI digestion, methylation at HhaI-site 2 results in the 4.7 fragment, whereas demethylation at HhaI-site 2 led to the 3.2 and the 1.5 fragments.

DETAILED DESCRIPTION OF THE INVENTION

Figure 1:
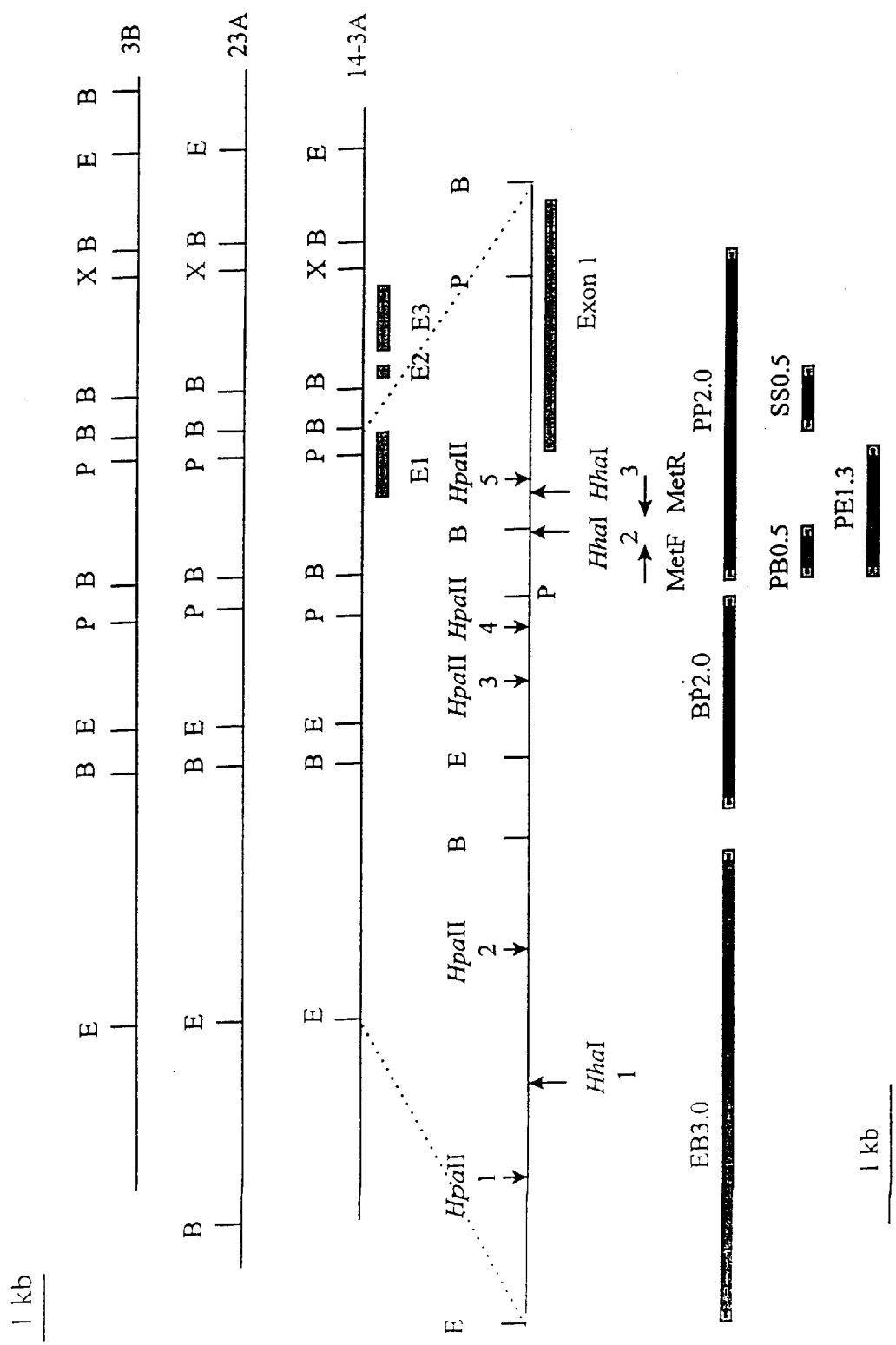
FIG. 1 shows the genomic structure of the cloned human MyoD1 gene. Three overlapping clones 3B, 23A, and 14-3A contain the MyoD1 upstream region and the entire coding region. The filled boxes below clone 14-3A show the location of the three exons. B: BamHI; E: EcoRI; X: XhoI; P: PstI. The region between the EcoRI and BamHI sites are enlarged to show the HpaII and HhaI sites. The relative positions of the MetF and MetR primers are indicated. The relevant HpaII and HhaI sites are designated by number. The positions of probes PP2.0 (SEQ ID No. 2), PB0.5 (SEQ ID No. 3), PE1.3 (SEQ ID No. 20), and SS0.5 (SEQ ID No. 4), derived from clone 14-3A, are shown.

The present invention reports the presence of methylation alterations in the 5' upstream region of the human MyoD1 gene from rhabdomyosarcomas. Abnormal methylation of the MyoD1 gene may be responsible for its persistent expression in rhabdomyosarcomas. The upstream CpG sites of the MyoD1 gene were methylated, at least on one copy of chromosome 11, in all adult muscle and non-muscle tissues examined. Hypomethylation of the upstream region was found in a large majority of alveolar rhabdomyosarcomas, which might account for the higher levels of the MyoD1 expression in this malignancy. The embryonal rhabdomyosarcomas presented with a partially methylated MyoD1 upstream region reminiscent of normal fetal muscle.

The methylation-sensitive PCR assay to determine the methylation status at particular sites within the 5' region of the MyoD1 gene provides a sensitive and specific diagnostic test that can be utilized in the clinical diagnosis and differentiation of rhabdomyosarcomas by allowing quick and reliable assessment of the methylation status of the MyoD1 upstream region. Since hypomethylation of the MyoD1 upstream CpG island was not found in any of the normal tissues, a negative PCR amplification would support the diagnosis of rhabdomyosarcoma. The correlation of hypomethylation of the MyoD1 CpG sites and high expression of the MyoD1 gene in rhabdomyosarcomas has therapeutic implications. If an unmethylated promoter can induce MyoD1 expression, as demonstrated by the transfection assays disclosed herein, then myogenesis may be induced in human non-myogenic cells and differentiated muscle cells by altering the methylation status of the MyoD1 CpG island to re-activate expression of the MyoD1 gene. This may provide a therapy for patients with muscular dystrophies and muscle injuries for whom skeletal muscle regeneration is desired. In accordance with the present invention there may be employed conventional molecular biology, microbiology, and recombinant DNA techniques within the skill of the art. Such techniques are explained fully in the literature. See, e.g., Maniatis, Fritsch & Sambrook, "Molecular Cloning: A Laboratory Manual (1982); "DNA Cloning: A Practical Approach," Volumes I and II (D. N. Glover ed. 1985); "Oligonucleotide Synthesis" (M. J. Gait ed. 1984); "Nucleic Acid Hybridization" [B. D. Hames & S. J. Higgins eds. (1985)]; "Transcription and Translation" [B. D. Hames & S. J. Higgins eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984). Therefore, if appearing herein, the following terms shall have the definitions set out below.

A "DNA molecule" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure herein according to the normal convention of giving only the sequence in the 5' to 3' direction along the nontranscribed strand of DNA (i.e., the strand having a sequence homologous to the mRNA).

A "promoter sequence", also referred to as a "5' upstream region" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include 1.5 kb. Within the promoter sequence will be found a transcription initiation site, as well as protein binding domains (consensus sequences) responsible for the binding of RNA polymerase. Eukaryotic promoters often, but not always, contain "TATA" boxes and "CAT" boxes. Prokaryotic promoters contain Shine-Dalgarno sequences in addition to the −10 and −35 consensus sequences. Promoter sequences often contain additional consensus sequences recognized by proteins involved in regulating expression of the respective gene. Regulation of gene expression by a promoter can occur by enhancing or inhibiting binding of a regulatory protein. Enhancing or inhibiting the binding or a regulatory protein can occur by many different means, including but not limited to, base modifications (i.e. methylation) and protein modification (i.e. phosphorylation).

The present invention comprises a vector comprising a DNA sequence corresponding to the 5' upstream region of the MyoD1 gene (SEQ ID No. 1); said vector is capable of replication in a host which comprises, in operable linkage: a) an origin of replication; and b) a DNA sequence coding for a protein. Preferably, the vector of the present invention contains a portion of the DNA sequence shown in SEQ ID No. 1, i.e., SEQ ID No. 2, SEQ ID No. 3, SEQ ID No. 4 and SEQ ID No. 20.

A "vector" may be defined as a replicable nucleic acid construct, e.g., a plasmid or viral nucleic acid. Vectors may be used to amplify nucleic acid containing the MyoD1 5' upstream region and/or express nucleic acid encoding a protein under the control of the MyoD1 5' upstream region. An "expression vector" is a replicable construct in which a nucleic acid sequence encoding a polypeptide is operably linked to suitable control sequences capable of effecting expression of the polypeptide in a cell. The need for such control sequences will vary depending upon the cell selected and the transformation method chosen. Generally, control sequences include a transcriptional promoter and/or enhancer, suitable mRNA ribosomal binding sites, and sequences which control the termination of transcription and translation. Methods which are well known to those skilled in the art can be used to construct expression vectors containing appropriate transcriptional and translational control signals. See for example, the techniques described in Sambrook et al., 1989, *Molecular Cloning: A Laboratory Manual* (2nd Ed.), Cold Spring Harbor Press, N.Y. A gene and its transcription control sequences are defined as being "operably linked" if the transcription control sequences effectively control the transcription of the gene. Vectors of the invention include, but are not limited to, plasmid vectors and viral vectors.

As used herein, the term "host" is meant to include not only prokaryotes but also eukaryotes such as yeast, plant and animal cells. A recombinant DNA molecule or gene which encodes a human MyoD1 5' upstream region of the present invention can be used to transform a host using any of the techniques commonly known to those of ordinary skill in the art. Especially preferred is the use of a vector containing the human MyoD1 5' upstream region of the present invention for purposes of prokaryote transformation. Prokaryotic hosts may include *E. coli, S. tymphimurium, Serratia marcescens* and *Bacillus subtilis.* Eukaryotic hosts include yeasts such as

*Pichia pastoris*, mammalian cells and insect cells. A cell has been "transformed" by exogenous or heterologous DNA when such DNA has been introduced inside the cell. The transforming DNA m ay or may not be integrated (covalently linked) into the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or ancestor by mitosis. A "cell line" is a clone of a primary cell that is capable of stable growth in vitro for many generations.

As used herein, the terms "restriction endonucleases" and "restriction enzymes" refer to enzymes, each of which cut double-stranded DNA at or near a specific nucleotide sequence. "Restriction site" is defined as the nucleotide sequence recognized by a specific restriction enzyme. The activity of certain restriction enzymes are dependent upon the modification or lack of modification of the substrate, such as the presence or absence of 5'-methylcytosine, and would therefore be referred to as "methylation-sensitive restriction enzymes".

A standard Southern blot assay can be used to ascertain the methylation pattern in the 5' upstream region of the MyoD1 gene in a cell or tissue obtained from a patient suspected of having cancer, in accordance with conventional Southern hybridization techniques known to those persons of ordinary skill in the art. This Southern assay uses a hybridization probe, e.g. radiolabelled fragments of the MyoD1 5' upstream region, single stranded DNA having a sequence complementary to SEQ ID No. 1, SEQ ID No. 2, SEQ ID No. 3 and SEQ ID No. 4, or a fragment of that DNA sequence at least 20 (preferably at least 30, more preferably at least 50, and most preferably at least 100 consecutive nucleotides in length). The DNA hybridization probe can be labelled by any of the many different methods known to those skilled in this art.

The labels most commonly employed for these studies are radioactive elements, enzymes, chemicals which fluoresce when exposed to untraviolet light, and others. A number of fluorescent materials are known and can be utilized as labels. These include, for example, fluorescein, rhodamine, auramine, Texas Red, AMCA blue and Lucifer Yellow. A particular detecting material is anti-rabbit antibody prepared in goats and conjugated with fluorescein through an isothiocyanate. Proteins can also be labeled with a radioactive element or with an enzyme. The radioactive label can be detected by any of the currently available counting procedures, or exposure to x-ray film, defined as "autoradiography". The preferred isotope may be selected from $^{3}$H, $^{14}$C, $^{32}$P, $^{35}$S, $^{36}$Cl, $^{51}$Cr, $^{57}$Co, $^{58}$Co, $^{59}$Fe, $^{90}$Y, $^{125}$I, $^{131}$I, and $^{186}$Re.

Enzyme labels are likewise useful, and can be detected by any of the presently utilized colorimetric, spectrophotometric, fluorospectrophotometric, amperometric or gasometric techniques. The enzyme is conjugated to the selected particle by reaction with bridging molecules such as carbodiimides, diisocyanates, glutaraldehyde and the like. Many enzymes which can be used in these procedures are known and can be utilized. The preferred are peroxidase, β-glucuronidase, β-D-glucosidase, β-D-galactosidase, urease, glucose oxidase plus peroxidase and alkaline phosphatase. U.S. Pat. Nos. 3,654,090, 3,850,752, and 4,016,043 are referred to by way of example for their disclosure of alternate labeling material and methods.

As used herein, the term "polymerase chain reaction" (PCR) is defined as a method of amplifying a specific region of DNA. This is done by combining the DNA of interest to be amplified, oligonucleotide primers, appropriate buffers, and a DNA polymerase. Amplification may be achieved by using a thermal cycler to control the length of time of each temperature fluctuation and the number of cycles. Amplification of DNA can be achieved by numerous methods which are known to one of skill in the art. The term "oligonucleotide", as used herein is defined as a molecule comprised of two or more deoxyribonucleotides, preferably more than three. Its exact size will depend upon many factors which, in turn, depend upon the ultimate function and use of the oligonucleotide. The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and use the method. For example, for diagnostic applications, depending on the complexity of the target sequence, the oligonucleotide primer typically contains 15–25 or more nucleotides, although it may contain fewer nucleotides.

The present invention is directed to DNA selected from the group consisting of: (a) isolated DNA which corresponds to the 5' upstream region of the MyoD1 gene; and (b) isolated DNA which hybridizes to isolated DNA of (a) above and which corresponds to the MyoD1 5' upstream region. Preferably, the DNA has the sequence shown in SEQ ID No. 1, SEQ ID No. 2, SEQ ID No. 3, SEQ ID No. 4 and SEQ ID No. 20.

The present invention is also directed to a vector containing the promoter of the present invention capable of expressing DNA in a recombinant cell and regulatory elements necessary for expression of DNA in a cell. Preferably, the vector contains DNA corresponding to the MyoD1 5' upstream region shown in SEQ ID No. 1, SEQ ID No. 2, SEQ ID No. 3 and SEQ ID No. 4.

The present invention is also directed to a host cell transfected with the vector described herein, said vector expressing a protein under control of the MyoD1 5' upstream region of the present invention. Representative host cells include consisting of bacterial cells, mammalian cells and insect cells.

The present invention is also directed to a method of detecting the methylation pattern of the 5' upstream region of the human MyoD1 gene, comprising the steps of: (a) restricting genomic DNA obtained from a cell with methylation-sensitive restriction enzymes and separating DNA by electrophoresis; (b) contacting genomic DNA with a labeled hybridization probe; and (c) detecting hybridization of the probe. Preferably, the probe consists of a portion of the DNA of SEQ ID No. 1, SEQ ID No. 2, SEQ ID No. 3, SEQ ID No. 4 and SEQ ID No. 20.

The present invention is also directed to a method of determining the methylation pattern of a MyoD1 5' upstream region in tissues of an individual in need of such determination, comprising the steps of: isolating genomic DNA from said tissues; and performing a methylation-sensitive PCR assay on said genomic DNA, wherein said methylation pattern is indicative of a neoplastic state of said tissues. In one embodiment, the methylation-sensitive PCR assay comprises the steps of: a) digesting said genomic DNA with a methylation-sensitive restriction enzyme to produce restricted DNA; b) amplifying said restricted DNA using DNA oligonucleotides flanking a methylatable restriction site to produce amplified products; and c) analyzing said amplified products, wherein absence of an amplified product indicates hypomethylation, and wherein presence of an amplified product indicates hypermethylation.

Using the method of the present invention, one may correlate the degree of methylation with disease state. For example, hypermethylated DNA is indicative of alveolar rhabdomyosarcoma, hypomethylated DNA is indicative of differentiated skeletal muscle tissue or normal non-muscle tissues, and partially methylated DNA is indicative of embryonal rhabdomyosarcoma. Although various methylation-sensitive restriction enzyme are possible, a typical example is HhaI. Representative examples of DNA oligonucleotides useful in performing this method include the DNA oligonucleotides have the sequence shown in SEQ ID No. 7 and SEQ ID No. 8. In one fashion, the methylatable restriction site corresponds to the HhaI restriction enzyme consensus sequence shown in SEQ ID No. 18 and corresponding to position −839 of SEQ ID No. 1, wherein the internal cytosine residue may be methylated. Preferably, the method is useful in analyzing tissues such as non-muscle cells, differentiated muscle tissue and myosarcomas. Generally, this method is useful in testing an individual suspected of having a soft-tissue cancer, a representative example of which is cancer is rhabdomyosarcoma.

The present invention is also directed to a kit having reagents in which to perform a methylation-sensitive PCR assay. Generally such a kit comprises reagents including buffers, DNA nucleotides and oligonucleotides, restriction enzymes, and conditions for optimal amplification.

The present invention is also directed to a method of distinguishing differentiated skeletal muscle tissue, fetal muscle tissue and myosarcoma tissue by determining the methylation pattern of the 5' upstream region of the MyoD1 gene, comprising the steps of: a) isolating genomic DNA from said tissue; b) digesting said genomic DNA with at least one restriction enzyme to produce restricted DNA; c) analyzing said restricted DNA by Southern blot, wherein the DNA probes used for hybridization are selected from the group shown by SEQ ID No. 2, SEQ ID No. 3, and SEQ ID No. 4, and wherein the digestion pattern is indicative of the extent of methylation of the 5' upstream region of the MyoD1 gene. Generally, the extent of methylation of the 5' upstream region of the MyoD1 gene is selected from the group consisting of hypermethylated DNA, hypomethylated DNA, and partially methylated DNA, hypermethylated DNA is indicative of alveolar rhabdomyosarcoma, hypomethylated DNA is indicative of differentiated skeletal muscle tissue or normal non-muscle tissues, and partially methylated DNA is indicative of embryonal rhabdomyosarcoma. Representative examples of restriction enzymes include: a) PstI alone and PstI/HhaI double digestion; b) MspI alone and HpaII alone; and c) HhaI alone, HpaII alone, and HhaI/HpaII double digestion.

The following examples are given for the purpose of illustrating various embodiments of the invention and are not meant to limit the present invention in any fashion.

EXAMPLE 1

Cloning and Sequencing of the Human MyoD1 Promoter Region

A human genomic EMBL3 SP6/T7 library (Clontech, Palo Alto, Calif.) was screened according to Maniatis et al by using a 114 bp PCR-amplified fragment that corresponds to nucletides 7–120 of the cDNA sequence of the human MyoD1 gene (Pearson-White, 1991). Primers M1 (5'-ACTGCCAGCACTTTGCAT-3') (SEQ ID No. 5) and M2 (5'-ATCCTGGCGGTGGCGCGGCA-3') (SEQ ID No. 6) were used in the PCR amplification. Overlapping restriction fragments derived from the positive phage clones were then subcloned into the pGEM3Zf(+) vector (Promega, Madison, Wis.) according to the manufacturer's instructions. Sequencing analysis was performed on both strands of the subcloned DNA with the fmol Cycle Sequencing System (Promega, Madison, Wis.). The sequencing products were analyzed using a 6% denaturing polyacrylamide gel. The gels were transferred onto blotting paper, dried, and exposed to Hyperfilm-MP (Amersham, Arlington Heights, Ill.) for 2–4 hours at −80° C.

EXAMPLE 2

DNA Isolation From Frozen Tumor Specimens and Normal Tissues and Southern Blot Analysis Frozen tumor material was obtained from St. Jude Children's Research Hospital (Memphis, Tenn.) and from a bank of tumor tissues derived from a previous Intergroup Rhabdomyosarcoma Study (IRS) (Parham et al., 1991). Diagnoses were obtained from previous IRS review or published retrospective analyses and were based on standard histologic criteria (Parham, 1994). Normal tissue specimens were obtained from Departments of Pathology at Arkansas Children's Hospital and The University of Arkansas for Medical Sciences (Little Rock, Ark.). All tissue samples were snap-frozen in liquid nitrogen-cooled isopentane immediately after surgical removal and stored at −80° C. until DNA extraction. Genomic DNA was extracted from snap-frozen rhabdomyosarcoma and normal tissue specimens with the Puregene DNA Extraction Kit according to the manufacturer's instructions (Gentra Systems, Inc., Minneapolis, Minn.). All procedures performed for handling the specimens were in agreement with the ethical standards of American College of Medical Genetics Storage of Genetics Materials Committee (American College of Medical Genetics, 1995).

The Southern blot methylation analysis was performed as described (Rideout et al, 1994; Tornaletti and Pfeifer, 1995; Southern, 1975). To analyze the methylation patterns of the MyoD1 gene, each DNA sample was digested by three groups of restriction enzymes: 1) PstI only or PstI plus HhaI; 2) MspI or HpaII; and 3) HhaI, HpaII, or HhaI plus HpaII. 5 $\mu$g each of normal and tumor DNA was separately digested with 40 U of HhaI, HpaII, MspI, PstI, 40 U each of PstI and HhaI, or 40 U each of HpaII and HhaI (New England Biolabs, Beverly, Mass.) at 37° C. for 16 h, followed by an additional 10 U of each enzyme for 8 h. The digested DNA fragments was separated by electrophoresis on 1.2% agarose gel, and blotted onto Hybond plus nylon membrane (Amersham, Arlington Heights, Ill.) overnight. The subcloned DNA fragments, PP2.0, PB0.5, and SS0.5, were used as probes for hybridization, and their locations relative to the MyoD1 gene are shown in FIG. 1. Approximately 100 ng of the plasmid insert DNA was $^{32}$P-labeled by random priming. All hybridizations were performed in 2× Denhardt's solution, 100 $\mu$g/ml denatured salmon sperm DNA, and 6× SSC at 65° C. for 24 h. Washing was performed at 65° C. in 3× SSC for 1 h, 2× SSC for 30 min, 1× SSC for 3 0 min, 0.5×

SSC for 30 min, and 0.1× SSC for 30 min. Then blots were exposed to Hyperfilm-MP (Amersham, Arlington Heights, Ill.) at −80° C. for 16 to 24 h.

EXAMPLE 3
Methylation-Sensitive Polymerase Chain Reaction (PCR)

1 μg each of normal or tumor DNA was digested with 1 0 U HhaI (New England Biolabs, Beverly, Mass.) at 37° C. for 16 hours, followed by an additional 1 U of the enzyme for 4 hours. The undigested DNA used as controls in the PCR amplification was prepared under the same conditions except that no HhaI was added to the reaction. Each reaction mixture consisted of 100 ng of DNA, 250 mM of each dNTP, 1.5 mM $MgCl_2$, 50 mM KCl, 5 pmol each of primers MetF (5'-CCGAGTTMGGAGAGATTGG-3') (SEQ ID No. 7) and MetR (5'-GACCCCGAGAGTTGAAGTG-3') (SEQ ID No. 8), and 2 U of Taq DNA polymerase (Perkin Elmer, Foster City, Calif.) in a total volume of 25 μl. Amplification was performed for all samples using 25 cycles of 94° C. for 30 sec, 55° C. for 30 sec, and 72° C. for 1 min. After amplification in a Perkin Elmer 9600 thermal cycler, the PCR products were electrophoresed through a 2% agarose gel containing 0.5 mg/ml ethidium bromide and photographed under UV light. All samples were analyzed at least twice in duplicate. The relative positions of primers used are shown in FIG. 1.

EXAMPLE 4
RNA Extraction and Reverse Transcriptase-PCR (RT-PCR)

Total RNA from normal muscle, rhabdomyosarcoma, and non-rhabdomyosarcoma specimens was extracted using the Purescript RNA Extraction Kit (Gentra Systems, Inc., Mineapolis, Minn.) following the manufacturer's instructions. The concentration of the extracted RNA was determined by spectrophotometry. For determining the relative levels of MyoD1 expression in embryonal and alveolar rhabdomyosarcomas, the first strand of cDNA was synthesized using the AMV reverse transcriptase (Gibco BRL, Gaithersburg, Md.) according to the manufacturer's instruction. The 20 μl mixture, containing 1 μg RNA, 40 U AMV reverse transcriptase, 100 pmol random hexamers (Amersham, Arlington Heights, Ill.), 40 U RNasin (Promega, Madison, Wis.) and 1 mM deoxyribonucleotide triphosphates (dATP, dCTP, dGTP, and TTP) in 10 mM Tris-HCl (pH 8.3) and a buffer containing 3 mM Na pyrophosphate, 50 mM Tris-HCl, 50 mM KCl, 0.5 mM spermidine, 10 mM DTT, and 10 mM $MgCl_2$, was incubated at 42° C. for 30 min and subsequently heated to 90° C. to denature the reverse transcriptase. The MyoD1 and the β-actin transcripts were simultaneously amplified using a pair of MyoD1 primers (M15: 5'-GCGGCGGAACTGCIGCGAA-3' (SEQ ID No. 9), and M16: 5'-GATGCGCTCCACGATGCTG-3' (SEQ ID No. 10)) and a pair of β-actin primers (ACTF: 5'-ACTCTTCCAGCCTTCCTT-3' (SEQ ID No. 11), and ACTR: 5'-CTCCTTCTGCATCCTGTC-3' (SEQ ID No. 12)), for 20 cycles at 94° C. for 30 sec, 55° C. for 30 sec, and 72° C. for 1 min. Then 1 μl of the 32 reaction mixture was end-labeled with $\gamma$-$^{32}$P-ATP, and electrophoresed through an 8% denaturing polyacrylamide gel for 1 hours at 30 W. The gel was dried, exposed to Hyperfilm (Amersham, Arlington Heights, Ill.) for 2–4 hours at room temperature, and analyzed with a BioRad Model GS-700 Imaging Densitometer by normalizing the intensity of the 115 bp MyoD1 PCR product to that of the 169 bp β-actin product.

For RT-PCR detection of the Pax3-FKHR or Pax7-FKHR fusion mRNA transcripts characteristic of alveolar rhabdomyosarcomas, synthesis of the first strand of cDNA w as performed as described (Friedman and Rosbash, 1977) with modification. The 20 μl mixture, containing 1 μg RNA, 200 U M-MLV reverse transcriptase (Gibco BRL, Gaithersburg, Md.), 100 pmol FKHR reverse primer (5'-ATTGAGCATCCACCAAGAAC-3' (SEQ ID No. 13)), 40 U RNasin (Promega, Madison, Wis.) and 1 mM deoxyribonucleotide triphosphates (dATP, dCTP, dGTP, and TTP) in 10 mM Tris-HCl (pH 8.3) and a buffer containing 50 mM KCl, 1.5 mM $MgCl_2$ and 0.001% gelatin, was incubated at 37° C. for 30 min and subsequently heated to 90° C. to denature the reverse transcriptase. PCR amplification was performed with the same FKHR reverse primer as used in the reverse transcription and a consensus primer Pax3/7 (5'-GACAGCAGCTCTGCCTAC-3' (SEQ ID No. 14)) which recognizes both Pax genes. This primer pair was predicted to amplify a 219 bp fragment for Pax3-FKHR and a 206 bp fragment for Pax7-FKHR. As a control, a parallel amplification reaction was performed by using the FKHR reverse primer and the FKHR forward primer (5'-GGTCAAGAGCGTGCCCTACT-3' (SEQ ID No. 15)) to amplify the normal FKHR transcript. The cycling parameters for both PCR reactions were 30 cycles of 94° C. for 30 sec, 55° C. for 30 sec, and 72° C. for 1 min. Then the entire PCR reaction was electrophoresed through a 10% native polyacrylamide gel for 3 hours at 200 V. The gel was stained in a solution of 1× TBE containing 1 μg/ml ethidium bromide, and photographed under UV light. To confirm the nature of the fusion genes, the samples that were positive for translocations were then amplified separately using the same FKHR reverse primer and a primer specific for the Pax3 gene (Pax3-specific: 5'-ACTGCCTCCCCAGCACCA-3' (SEQ ID No. 16)), or a primer specific for the Pax7 gene (Pax7-specific: 5'-TTCTCCAGCTACTCTGAC-3' (SEQ ID No. 17)). All primers were selected by the software Oligo 4.0 based on the published FKHR, Pax3-FKHR, and Pax7-FKHR coding sequences.

EXAMPLE 5
Cell Culture. DNA Transfection, and Promoter Activity Assay

SJRH30, a human rhabdomyosarcoma cell lines, and CCL-136, a human embryonal rhabdomyosarcoma cell line, were purchased from the American Tissue Culture Collection (Rockville, Md.). NIH3T3 cell line was from Dr. M. You (Medical College of Ohio, Toledo, Ohio). Cells were cultured in Dulbecco's modified Eagle's medium supplemented with 10% fetal bovine serum (Gibco BRL, Gaithersburg, Md.). Approximately 1×10⁵ cells were plated in 60 mm culture flasks 24 hours prior to transfection by using the calcium phosphate method. The calcium phosphate/DNA precipitate was formed in a total volume of 600 μl and consisted of 10 μg of pGL3 reporter plasmid (Promega, Madison, Wis.) and 1 μg of the SEAP control plasmid (Clontech, Palo Alto, Calif.). The DNA precipitate was removed the following day and the cells washed in PBS prior to being re-fed with fresh media. After 48 hours, the cells were harvested and assayed for luciferase activity. Transfection efficiency was normalized relative to the secreted alkaline phosphatase (SEAP) activity determined in the culture medium as described by the manufacturer. Each experiment was repeated at least three times in duplicate, and the variation between experiments was less than 10%.

EXAMPLE 6
The Human MyoD1 Gene

Of approximately 3×10⁵ phage clones screened, three overlapping clones, 3B, 23A, and 14-3A, were identified that contained the exon 1 sequence of the human MyoD1 gene. A restriction map was constructed, and the genomic structure of the cloned MyoD1 gene is shown in FIG. 1. Sequence analysis of the clones did not reveal any difference to the published human MyoD1 cDNA sequence (Pearson-White, 1991), except for the presence of the 5' and 3' noncoding regions and the two introns.

The nucleotide sequence of the 1.5 kb 5' upstream region and part of the first exon is shown in FIG. 2. As compared to the MyoD1 structural gene which is defined as a CpG island, the 1.5 kb upstream region is relatively GC rich (60% G+C) and contains 69 CpG sequences. Analysis of this region revealed highly conserved elements typical for eukaryotic promoters that are recognized by RNA polymerase II. A potential TATA-box is located at –126 relative to the transcription start site, and a potential CAAT-box was found at –190. Except for the potential TATA- and CAAT-boxes, which bear 100% identity to that found in the promoter region of the mouse MyoD1 gene, no significant sequence conservation between human and mouse was found within the upstream regions. In addition, an AP1 site, 10 AP2 binding sites, a CRE site, and 7 bHLH binding sites for MyoD1 and its relatives were identified. A 10 bp sequence is found at –578 which is highly homologous to a core Pax3-binding site identified in the promoter region of the c-Met proto-oncogene (Epstein et al, 1996).

EXAMPLE 7
Methylation Pattern of the MyoD1 Gene in Normal Muscle Tissue and Non-Myogenic Tissues The methylation pattern of the MyoD1 gene was examined in normal skeletal muscle (N=6) and non-muscle tissues, including liver (N=4), lung (N=4), pancreas (N=3), peripheral lymphocytes (N=20), heart (N=3), kidney (N=3), and spleen (N=2), by Southern blot analysis utilizing the methylation-sensitive restriction enzymes HhaI and HpaII. Methylation of the HhaI recognition site GCGC (SEQ ID No. 18) at the internal cytosine residue inhibits the enzyme digestion. Similarly, the presence of an internal 5-methylcytosine residue in the HpaII site CCGG (SEQ ID No. 19) prevents HpaII digestion. MspI is the methylation-insensitive isozyme of HpaII and digests DNA whether the internal CpG is methylated or not. Therefore, MspI digestion was used as a control for HpaII digestion, as the difference would reflect CpG methylation of the DNA being analyzed. Since the 2 kb PstI fragment contains 28 HhaI sites, the PstI enzyme was used in combination with HhaI to assess the methylation status of the 2 kb sequence containing 1.4 kb upstream region and the first 602 bp of exon 1 of the MyoD1 gene. With no methylation, two fragments of 580 bp and 420 bp, as well as several smaller fragments below 200 bp, would result from the double digestion. However, if there is 5' CpG methylation, larger restriction fragment(s) would be generated.

Figure 3A:
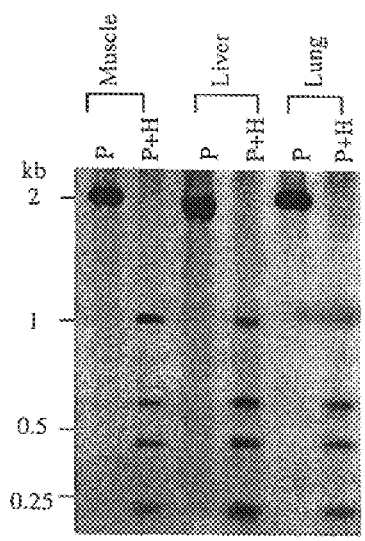
FIG. 3A: PstI only or PstI/HhaI double digestion, hybridized to the 2 kb PstI fragment (probe PP2.0, SEQ ID No. 2).
Figure 3B:
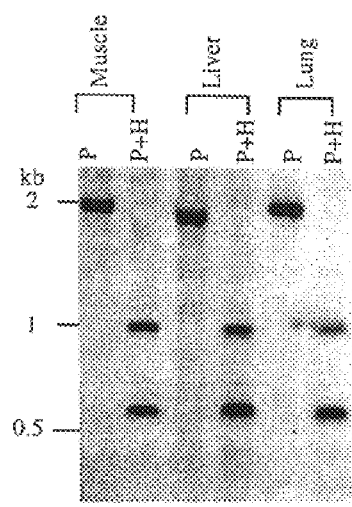
FIG. 3B: The same blot was stripped and hybridized to the 556 bp PstI-BamHI fragment (probe PB0.5, SEQ ID No. 3). Notice the presence of the methylated 1 kb band in both hybridizations.
Figure 3C:
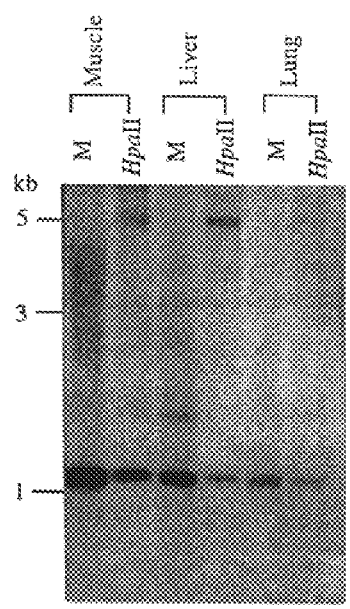
FIG. 3C: MspI or HpaII digestion, hybridized to probe PP2.0 (SEQ ID No. 2). A 5 kb band is present in all HpaII digestions, indicating the hypermethylated CpG island. P: PstI digestion; P+H: PstI and HhaI double digestion; M: MspI digestion.
Figure 4A:
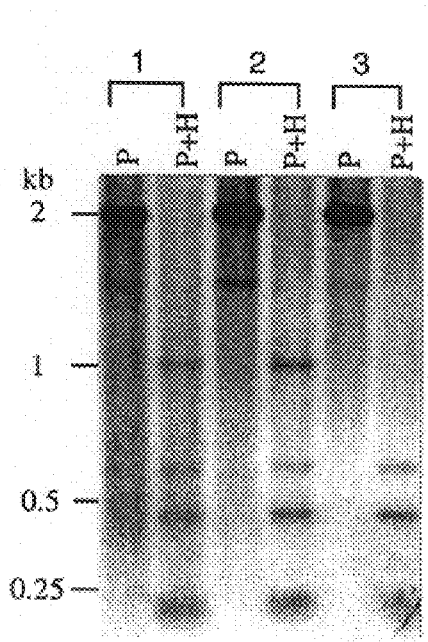
FIG. 4A: PstI or PstI/HhaI double digestion, hybridized to the 2 kb PstI fragment (probe PP2.0, SEQ ID No. 2). 1: a peripheral lymphocyte sample; 2: a normal skeletal muscle sample; and 3: an alveolar rhabdomyosarcoma.
Figure 4B:
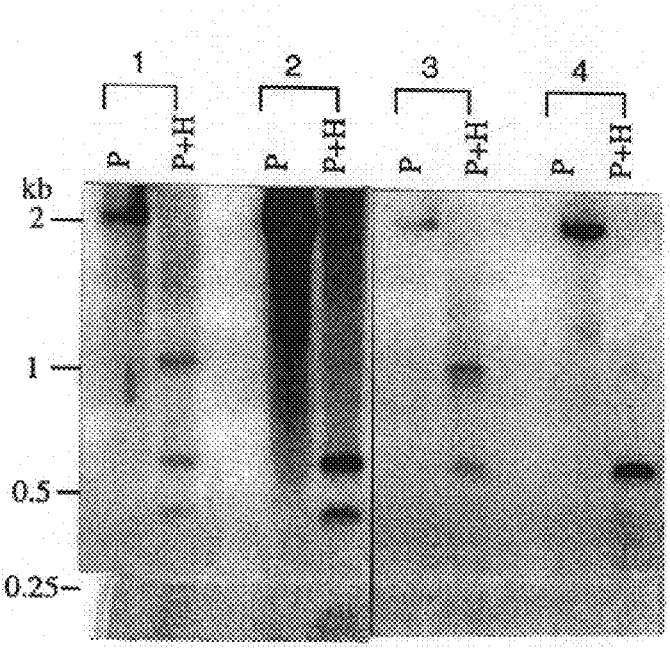
FIG. 4B: A comparison between hybridizations with probe PP2.0 and probe PB0.5 (SEQ ID No. 3). 1 and 3: an embryonal rhabdomyosarcoma; 2 and 4: an alveolar rhabdomyosarcoma. The DNA samples were digested with PstI or PstI and HhaI, and hybridized to probe PP2.0 (1 and 2). The same blot was stripped and then hybridized to probe PB0.5, shown by 3 and 4.
Figure 4C:
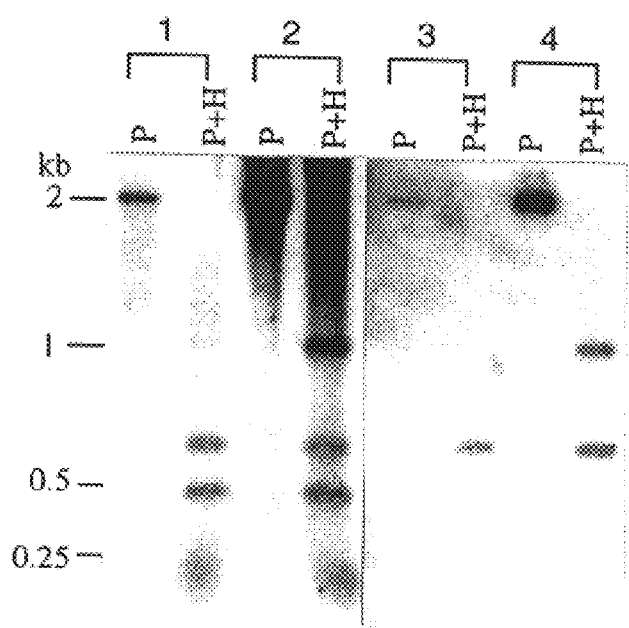
FIG. 4C: DNA from an alveolar rhabdomyosarcoma (1 and 3) and a normal cardiac muscle sample (2 and 4), digested with PstI or PstI and HhaI and hybridized to either probe PP2.0 (1 and 2) or probe PB0.5 (3 and 4). Notice the absence of the 1 kb PstI/HhaI band from all 3 alveolar rhabdomyosarcomas.
Figure 4D:
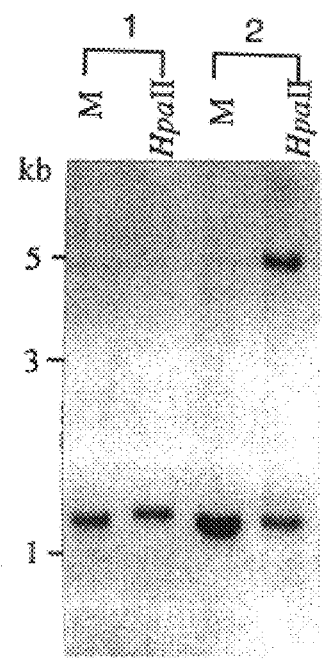
FIG. 4D: MspI or HpaII digestion of an alveolar rhabdomyosarcoma (1) and an embryonal rhabdomyosarcoma (2), hybridized to probe PP2.0. Notice that the 5 kb band representing the hypermethylated CpG island is absent in the alveolar tumor but present in the embryonal rhabdomyosarcoma. P: PstI digestion; P+H: double digestion by PstI and HhaI; and M: MspI digestion.

Upon PstI/HhaI double digestion, DNA samples from all normal tissues showed three discrete bands, approximately 1 kb, 0.6 kb, and 0.4 kb, when the 2 kb PstI fragment (PP2.0, SEQ ID No. 2) was used as a hybridization probe (FIG. 3, panel A). Since the 1 kb fragment was larger than any derivative fragment predicted for the double digestion, hypermethylation of the MyoD1 gene could b e present in the normal tissues studied. To test which CpG site(s) was methylated leading to the failure of HhaI digestion, the same blots were stripped and re-hybridized to a 556 bp PstI-BamHI fragment (PB0.5, –1417 through –861, SEQ ID No. 3). As shown in FIG. 3B, the new probe hybridized to both the 1 kb and the 0.6 kb bands but not to the 0.4 kb fragment (FIG. 3, panel B). Since probe PB0.5 resides entirely in the 0.58 kb PstI-HhaI fragment (–1417 though –839), the 1 kb band on both hybridizations must consist of nt –1417 through –422, generated due to CpG methylation of the HhaI site number 2 at –839 (FIG. 1).

To test if methylation involved the MyoD1 coding sequence, a 565 bp SmaI fragment (SS0.5, –229 through +336, SEQ ID No. 4) was then used as the hybridization probe. Despite the presence of the 2 kb fragment from the PstI only digestions, none of the three fragments were detectable from the PstI/HhaI double digestions, suggesting that hypermethylation did not extend to the CpGs of the multiple HhaI sites in exon 1 of the MyoD1 gene.

The methylation status of the MyoD1 gene in normal tissues was also analyzed with enzymes MspI and HpaII. HpaII is a methylation sensitive restriction enzyme which does not digest DNA when the internal C of its recognition sequence (CCGG, SEQ ID No. 19) is methylated. MspI, an isozyme of HpaII, is insensitive to the methylation of the internal C and digests DNA even when the CpG island is methylated. Therefore, MspI digestion acts as a good control for HpaII digestion, and the difference between them reflects CpG methylation of the DNA being analyzed. As shown in FIG. 1, barring CpG methylation, two larger fragments of 1.2 kb and 300 bp, as well as several smaller fragments below 200 bp, would result from digestion by either MspI or HpaII. However, if the MyoD1 upstream region is hypermethylated, larger restriction fragment(s) would be produced in HpaII digestions.

In all normal tissue DNAs examined, hypermethylation of the 5' upstream region was revealed by the presence of a 5 kb HpaII fragment in addition to the 1.2 kb band observed also in all MspI digestions (FIG. 3, panel C). This hybridization pattern remained unchanged whether PP2.0 (SEQ ID No. 2), PB0.5 (SEQ ID No. 3), or the 2.4 kb BamHI fragment was used as a probe. However, when the SS0.5 (SEQ ID No. 4) was used to probe the same blots, neither the 5 kb nor the 1.2 kb band was detectable. These results indicated that 1) a CpG island as long as 5 kb is present in the 5' upstream region of the MyoD1 gene; and 2) the upstream CpG island is methylated in normal skeletal muscle cells and in normal non-myogenic cells.

Figure 6:
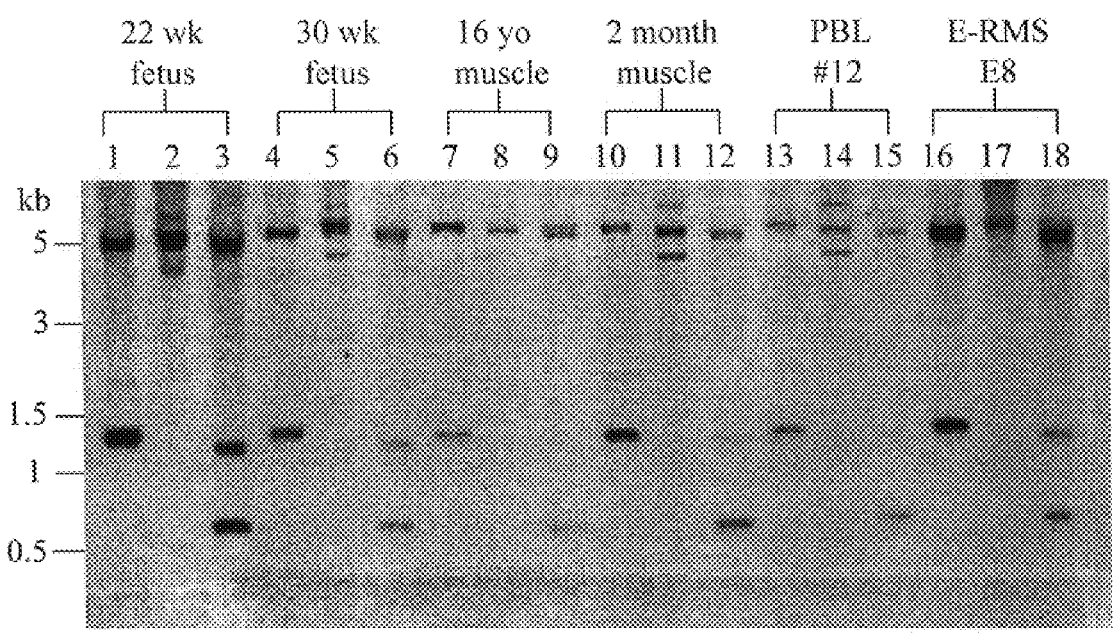
FIG. 6 shows the partial methylation of the MyoD1 upstream region in embryonal rhabdomyosarcomas and in fetal muscle. Lanes 1, 4, 7, 10, 13, and 16: HpaII digestion; lanes 2, 5, 8, 11, 14, and 17: HhaI digestion; and lanes 3, 6, 9, 12, 15, and 18: HpaII/HhaI double digestion. Each lane contained 5 jig digested DNA. The blot was hybridized to the 556 bp PstI-BamHI fragment (probe PB0.5, SEQ ID No. 3). Notice that the 1.1 kb band was present in the embryonal tumor DNA and in the fetal muscle DNAs, but not in adult muscle or peripheral lymphocyte DNA samples following HpaII/HhaI double digestion.

EXAMPLE 8
The MyoD1 Upstream Region is Partially Methylated in Embryonal Rhabdomyosarcomas and Normal Fetal Muscle Tissues Fourteen embryonal rhabdomyosarcomas were studied for MyoD1 methylation. PstI/HhaI or HpaII digestions did not show significant methylation differences between tumors and the normal tissues. To learn more about the distribution of methylated CpGs along the MyoD1 upstream region, an HhaI/HpaII double digestion was performed to test if the methylated HpaII sites were located on the same DNA strand as the methylated HhaI sites. In all non-muscle tissues and 6 adult muscle specimens, the methylated HpaII and HhaI sites were on the same DNA strand, evidenced by the persisting 5 kb band and a 666 bp fragment which could b e generated only by HhaI/HpaII digestion of a DNA strand unmethylated at the HpaII site number 4 at –1505 and the HhaI site number 2 at –839 (FIG. 6). However, a different pattern was observed for fetal muscle DNA samples, all of which showed a novel fragment approximately 1.1 kb, in addition to the 666 bp and the 5 kb fragment. Subsequent hybridizations using probes PP2.0, PB0.5, and SS0.5 showed that this novel band was the 1081 bp fragment from the HpaII site number 4 at –1505 through the HhaI site number 3 at –424, a result of digestion at an unmethylated HpaII site number 4 at –1505 on a DNA strand that carries a methylated HhaI site number 2 at –839. Therefore, partially methylated MyoD1 upstream DNA is present in cells from normal fetal muscles, which presumably represents an earlier developmental stage in relation to the adult muscle specimens, consisting primarily of differentiated myotubes.

Upon HhaI/HpaII digestion, 13 of 14 embryonal tumors had a hybridization pattern indistinguishable from that of the normal fetal muscles (represented by E-RMS #E8 in FIG. 6). Therefore, embryonal rhabdomyosarcoma, which bears histologic resemblance to fetal muscle tissue, had a partially methylated MyoD1 upstream region reminiscent of fetal muscle but distinct from differentiated muscle and non-muscle cells.

Figure 7A:
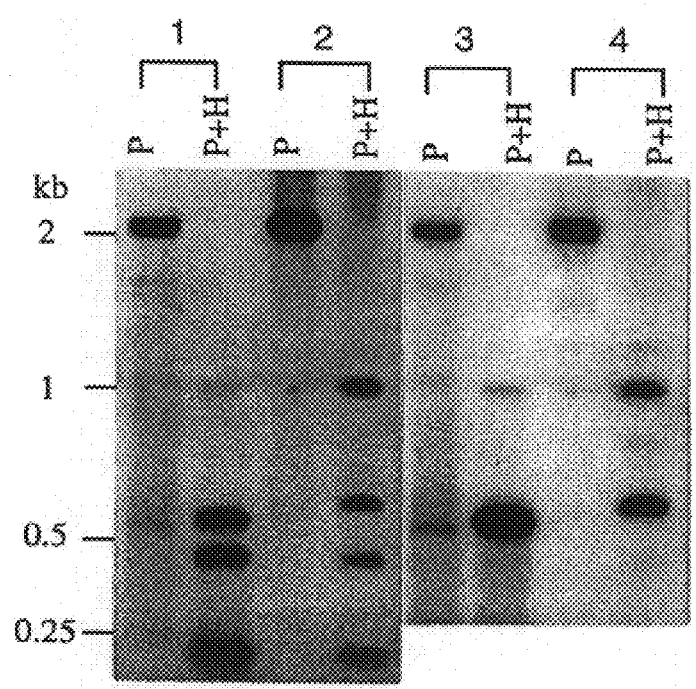
FIG. 7A: PstI or PstI/HhaI double digestion, hybridized to probe PP2.0 (SEQ ID No. 2). 1: The 0.6 kb band is replaced by a smaller fragment in one embryonal rhabdomyosarcoma. A very weak 1 kb band is present for this tumor, most likely a result of contamination by adjacent normal tissue. 2. Another embryonal rhabdomyosarcoma that shows the hypermethylated 1 kb band. 3 and 4: The same blot was stripped and hybridized to probe PB0.5 (SEQ ID No. 3).
Figure 7B:
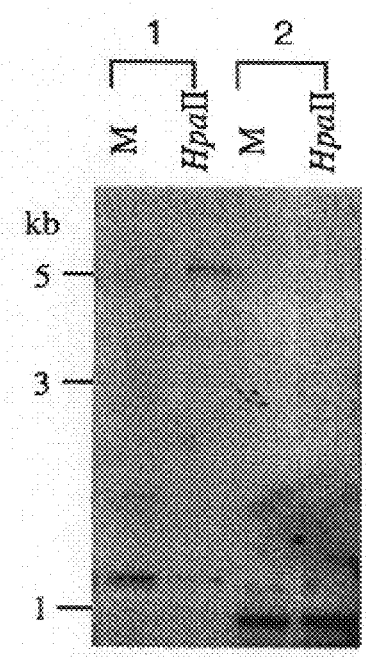
FIG. 7B: MspI or HpaII digestion, hybridized to probe PP2.0. 1: An embryonal rhabdomyosarcoma; and 2: The embryonal rhabdomyosarcoma that shows partial deletion in FIG. 7A. Notice the absence of the 5 kb hypermethylated band and the replacement of the 1.2 kb band with a novel 1 kb fragment in this tumor. P: PstI digestion; P+H: PstI and HhaI double digestion; and M: MspI digestion.
Figure 8:
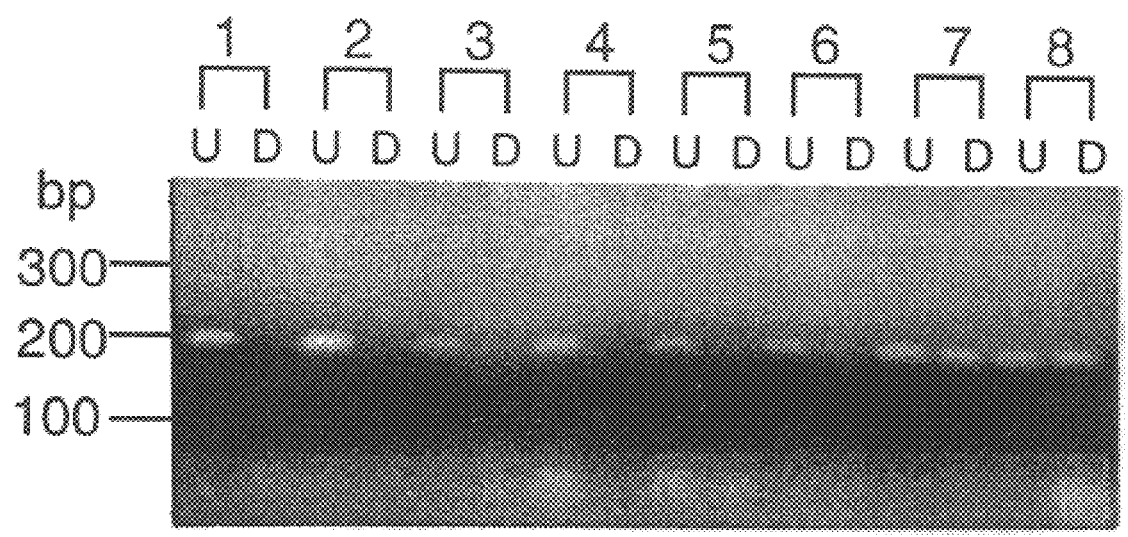
FIG. 8 shows the detection of the CpG hypomethylation in alveolar rhabdomyosarcomas by a methylation-sensitive PCR assay. Lanes 1–6: 6 alveolar rhabdomyosarcomas; lane 7: an embryonal rhabdomyosarcoma; and lane 8: a normal skeletal muscle sample. U: amplified with undigested DNA. D: amplified with HhaI digested DNA. After PCR amplification, the reactions were electrophoresed through a 2% agarose gel and visualized under UV light.

In one embryonal rhabdomyosarcoma, a short deletion, together with hypomethylation of the upstream CpG sites, was found in the MyoD1 gene. The deletion in this tumor is evidenced by an approximate 1 kb instead of the normal 1.2 kb band upon MspI or HpaII digestion (FIG. 7, panel B). The deletion was also detected with the PstI/HhaI digestion by the replacement of the usual 0.6 kb fragment with a novel 0.5 kb band (FIG. 8, panel A).

EXAMPLE 9
Hypomethylation of the MyoD1 Upstream Region in Rhabdomyosarcomas and Detection of the MyoD1 Hypomethylation in Alveolar Rhabdomyosarcomas by A Methylation-Sensitive PCR Assay The methylation status of the upstream CpG island in 33 rhabdomyosarcomas was studied with Southern blot analysis by using the same methylation-sensitive enzymes as described for the normal tissues. Hypomethylation of the MyoD1 upstream CpG sites was found in a majority (13/15, 87%) of alveolar rhabdomyosarcomas examined, revealed both by the absence of the 1 kb band upon the PstI/HhaI digestion (FIGS. 4, panels A and B) and by the absence of the 5 kb band upon the HpaII digestion (FIG. 4, panel C).

Figure 5:
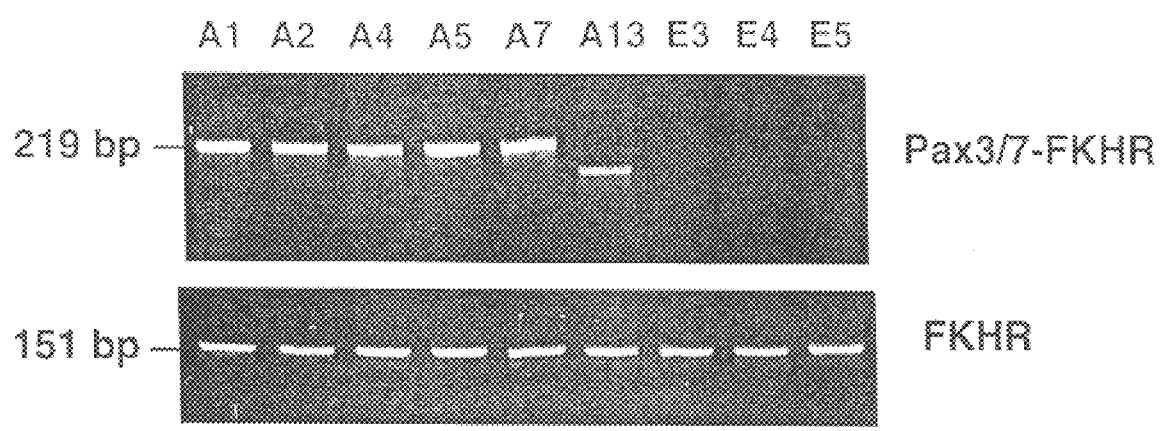
FIG. 5 shows the RT-PCR analysis of the Pax3-FKHR or Pax7-FKHR fusions in alveolar rhabdomyosarcomas. Six alveolar (lanes 1–6) and 3 embryonal (lanes 7–9) rhabdomyosarcomas were analyzed and the tumor numbers are shown above the gel. Tumors in lanes 1–5 presented with a 219 bp amplification product indicating the Pax3-FKHR fusion, while the tumor in lane 6 showed a smaller PCR product consistent with the Pax7-FKHR fusion. The normal FKHR mRNA was amplified for each tumor as a control.

To confirm the histological diagnosis of alveolar rhabdomyosarcoma and to show the relationship between the MyoD1 CpG hypomethylation and the tumor-specific chromosomal translocations, t(2;13) and t(1;13), in this tumor type, RNA isolated from these tumors was examined for the presence of the Pax3-FKHR or the Pax7-FKHR transcripts by using an RT-PCR analysis. Of the 13 tumors that showed CpG hypomethylation, 12 were positive for the Pax3-FKHR or the Pax7-FKHR fusion mRNA transcripts (FIG. 5). The two alveolar tumors that did not show MyoD1 CpG hypomethylation were negative for the chromosomal translocations by RT-PCR.

Southern blot analyses on both normal tissues and rhabdomyosarcomas indicates that the 1 kb fragment upon PstI/HhaI digestion is a result of the methylation of the HhaI site number 2 at nt −839; whereas in the majority of alveolar rhabdomyosarcomas, this HhaI site is unmethylated, leading to enzymatic digestion. To illustrate the diagnostic utility of this finding, a PCR assay was developed based on the methylation status of the internal Cin the HhaI site number 2 at −839. When this CpG site is methylated, as occurs in normal tissues and embryonal rhabdomyosarcomas, the DNA template would be protected from HhaI digestion and would lead to PCR amplification by extension of the two primers that flank the HhaI site number 2. On the other hand, in alveolar rhabdomyosarcoma, the -839 HhaI site number 2 is unmethylated on both copies of the MyoD1 gene. Therefore, in alveolar rhabdomyosarcoma, no amplification would result since the DNA template is disrupted by HhaI digestion. Under these conditions, none of the 13 tumors with MyoD1 CpG hypomethylation showed detectable amplification, whereas all normal tissue and 17/18 embryonal rhabdomyosarcoma DNA samples presented with PCR products of predicted size (FIG. 8).

Figure 9:
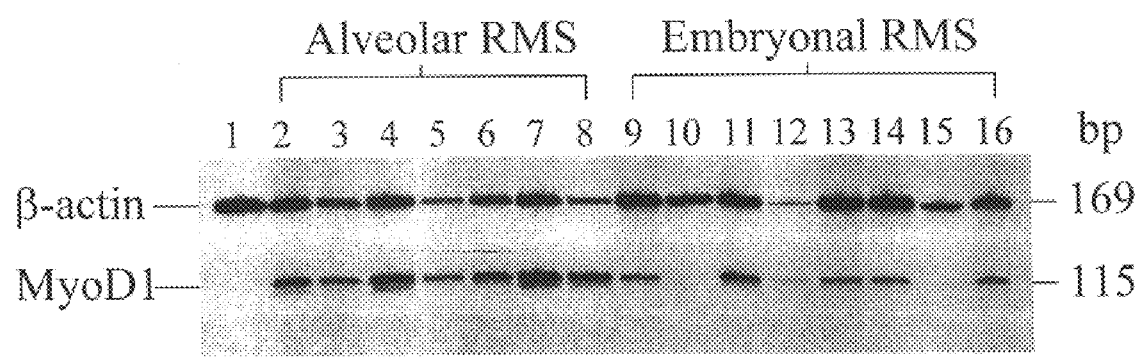
FIG. 9 shows the level of MyoD1 expression in rhabdomyosarcomas using RT-PCR.

EXAMPLE 10
Hypomethylation of the Upstream CpG Sites is Associated with Higher Levels of MyoD1 Expression in Rhabdomyosarcomas In order to determine whether the different methylation patterns in the MyoD1 upstream region are correlated with the levels of the gene expression in alveolar and embryonal rhabdomyosarcomas, RNA was extracted from tumors of both subtypes, and MyoD1 expression assessed by an RT-PCR assay. A total of 11 alveolar rhabdomyosarcomas and 12 embryonal rhabdomyosarcomas were analyzed. After normalizing to the co-amplified β-actin signals, the intensity of the MyoD1 transcripts in alveolar rhabdomyosarcomas was 4–10 times higher, relative to the that in the embryonal rhabdomyosarcomas (FIG. 9). Therefore, greater MyoD1 expression was found in alveolar rhabdomyosarcomas in relation to tumors of the embryonal subtype, consistent with the distinct methylation patterns of the MyoD1 gene in the two tumor subtypes.

EXAMPLE 11
Inactivation of the MyoD1 Promoter by CpG Methylation

Figure 10:
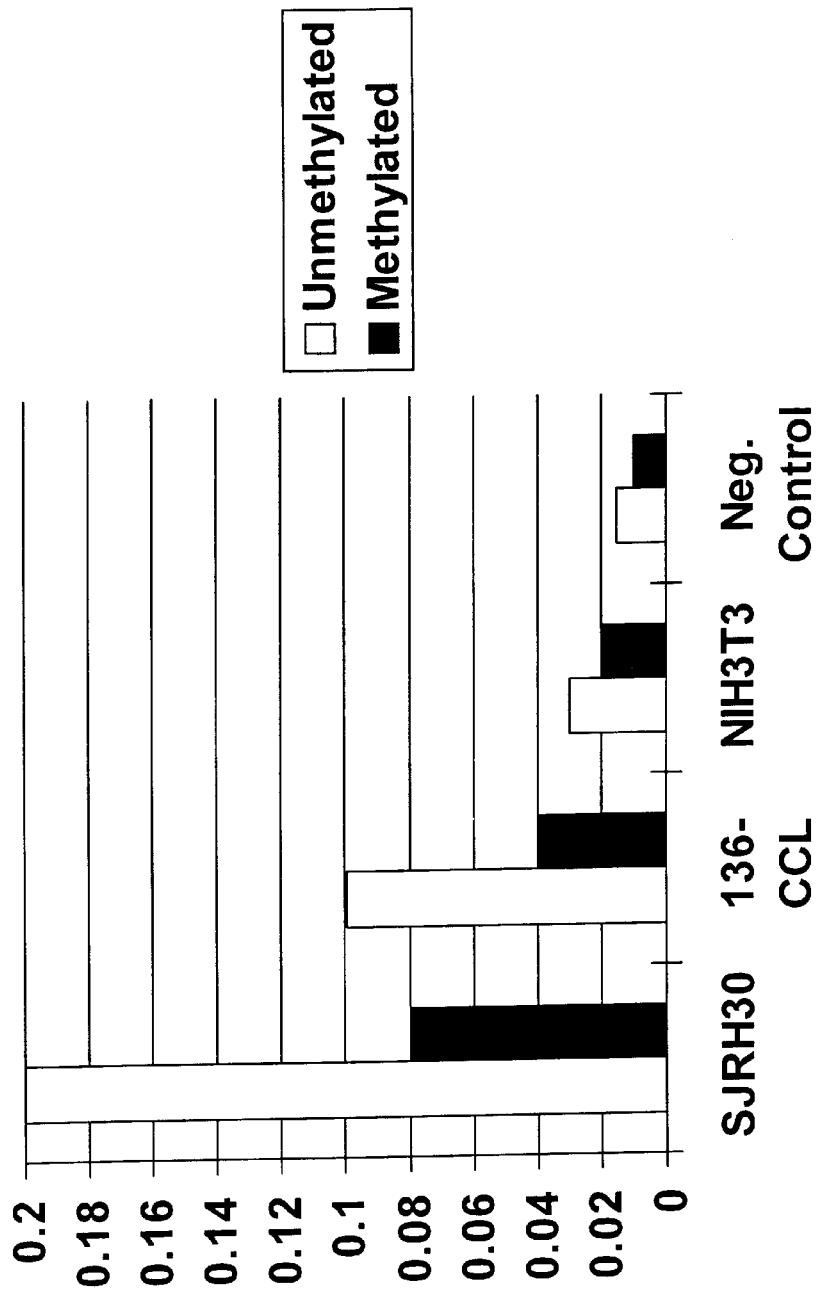
FIG. 10 shows the inactivation of the MyoD1 promoter due to CpG methylation as measured by luciferase reporter gene activity.

The cloned 1.4 kb upstream region of the MyoD1 gene was tested for promoter activity by transient transfection of MyoD1-luciferase fusion constructs into an alveolar rhabdomyosarcoma cell line SJRH30, an embryonal rhabdomyosarcoma cell line 136-CCL, or NIH3T3 cells. The transfection plasmid was constructed by inserting a 1.3 kb PstI-EheI fragment (PE1.3, see FIG. 1) in the multiple cloning region of a pGL3 enhancer vector. The MyoD1-luciferase constructs yielded about 20% of luciferase activity in transfected SJRH30 cells and 10% activity in 136-CCL and NIH3T3 cells, compared to that detected with the SV40 early promoter of the pGL3 control plasmid (FIG. 10). The results were normalized to the SEAP activity in the culture media and to the exogenous MyoD1 DNA content in the transfected cells. In order to show the effect of methylation on the promoter activity of the 1.4 kb sequence, the MyoD1-luciferase fusion constructs were transfected into SJRH30 or 136CCL cells in the methylated form. As shown in FIG. 10, methylation of the reporter vector by CpG methylase SssI resulted in a greater than 50% decrease of MyoD1 promoter activity in both alveolar and embryonal tumor cells. This indicated that at least in vitro, transcription of the MyoD1 gene could be inhibited by CpG methylation of the 5' upstream region.

The ability of 5-azacytidine to reactivate a silent MyoD1 gene in mouse fibroblasts (Konieczny and Emerson, 1984) suggest that DNA methylation may play a specific role in regulating MyoD1 expression. The present invention demonstrated that at least in alveolar rhabdomyosarcoma, hypomethylation of the MyoD1 upstream CpG sites is associated with enhanced gene expression. Moreover, these results determined that there were major positive regulatory elements in the 1.4 kb upstream region.

Figure 11:
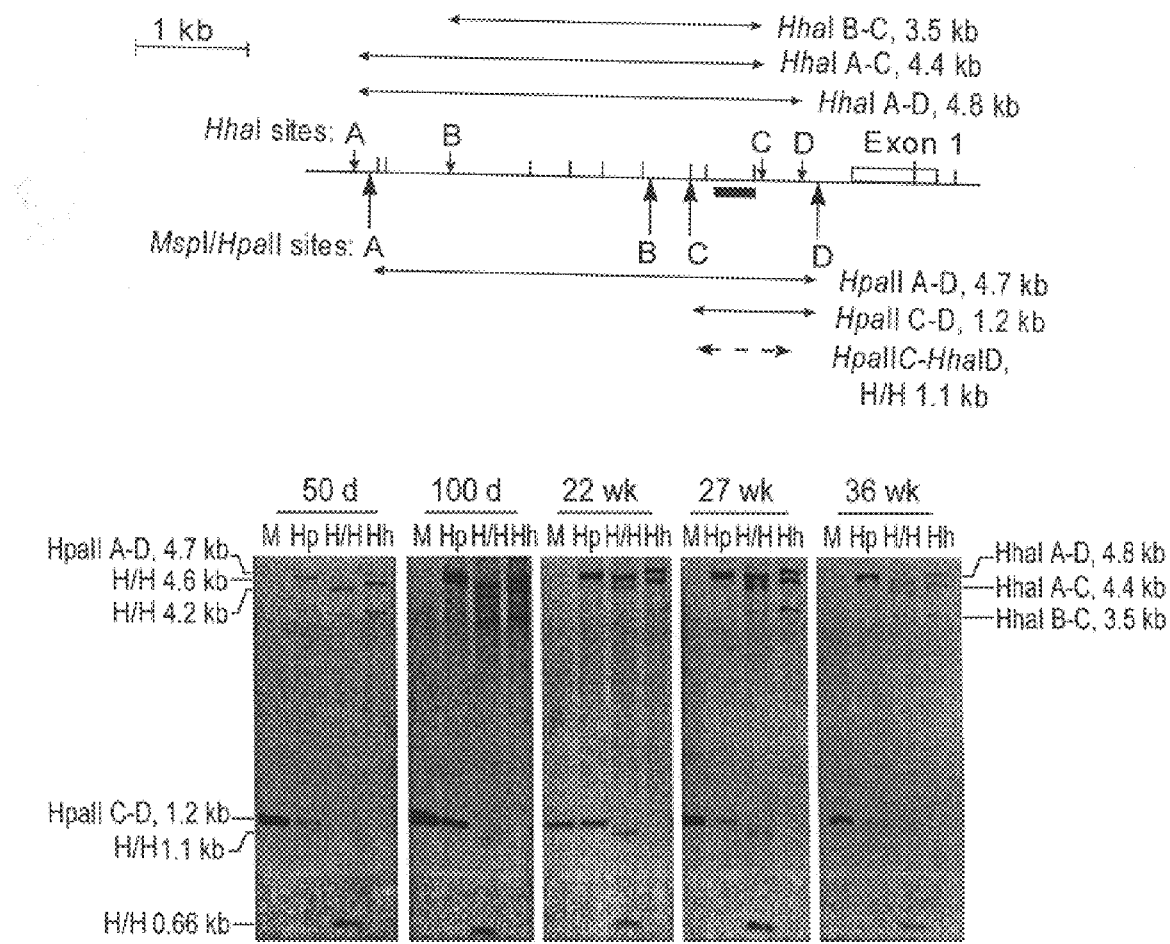
FIG. 11 shows progressive methylation in the MyoD1 immediate upstream region during fetal myogenesis.

EXAMPLE 12
Progressive CpG Methylation at the 5' Upstream Region of the Human MyoD1 gene during Skeletal Muscle Differentiation Methylation state of the MyoD1 upstream region was studied by Southern blot analysis using normal skeletal muscle DNA from 50-day to 36-week fetuses. Progressive CpG methylation was observed both in the immediate upstream region (FIG. 11) and the enhancer (FIG. 12) of the MyoD1 gene during the course of fetal development. In the immediate upstream region, upon digestion by a methylation-sensitive restriction enzyme HhaI, a 4.4-kb fragment (HhaI A–C) is observed if HhaI-site C is unmethylated and only HhaI-site B is methylated, whereas a 4.8-kb fragment (HhaI A–D) appears if both HhaI-sites B and C are methylated. As shown in FIG. 11, the intensity of the 4.8 kb HhaI A–D fragment increased while the relative intensity of the 4.4 kb HhaI A–C fragment decreased in skeletal muscle DNA from 50 day-36 week-old fetuses, indicating progressive methylation at HhaI-site C. This observation is also supported by double digestion with HhaI and another methylation-sensitive enzyme HpaII (H/H), in which the presence of a 1.1-kb fragment in 100-day to 27-week muscle DNA indicated methylation of HhaI-site C on an allele with unmethylated HpaII-site C (FIG. 11, HpaII-HhaI, 1.1 kb). The 1.1-kb band is also observed in 30-week fetal muscle DNA, but is absent in skeletal muscle after birth due to complete methylation at both HpaII-site C and HhaI-site C.

Figure 12:
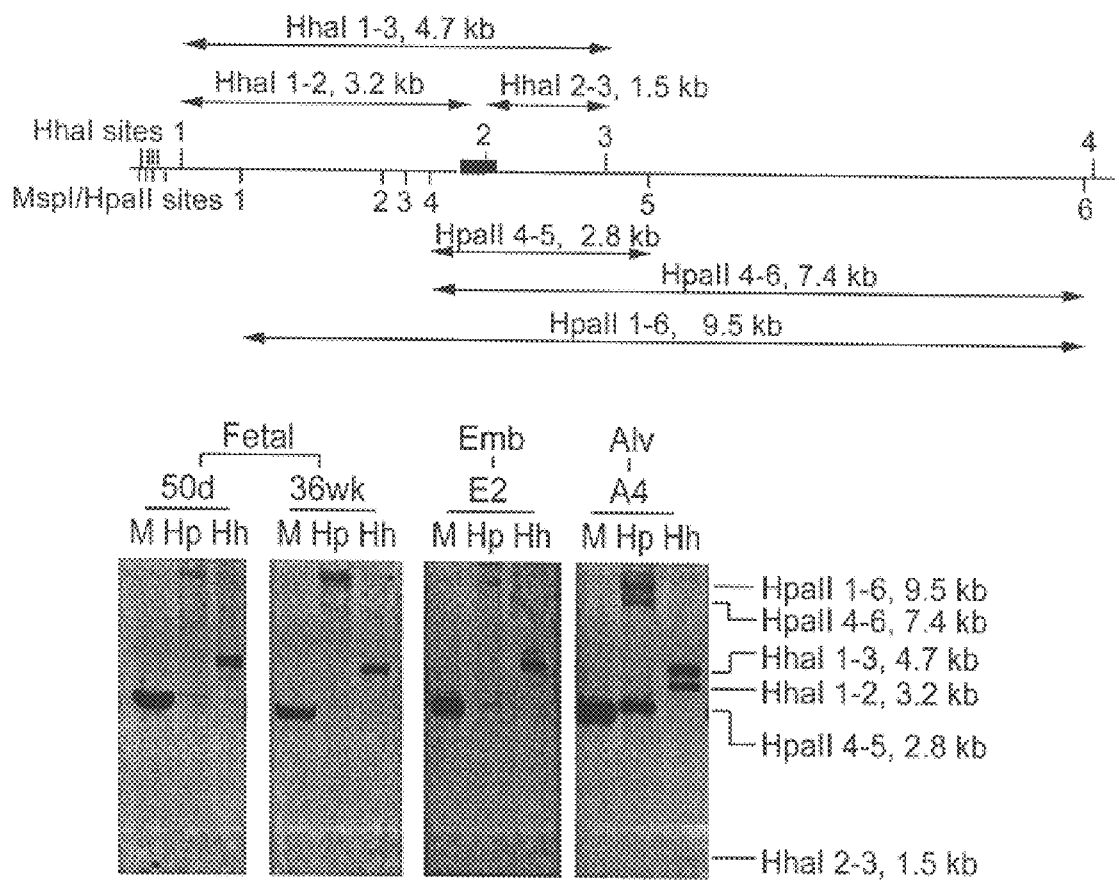
FIG. 12 shows progressive CpG methylation in the MyoD1 enhancer region in normal fetal muscle (50 day- and 3 6 week-old) and demethylation in embryonal (Emb) and alveolar (Alv) rhabdomyosarcoma.

A similar dynamic methylation progress was found during fetal development at the MyoD1 enhancer region, which is located at 20 kb upstream of the coding region (FIG. 12). Upon HpaII digestion, a 2.8-kb fragment (HpaII 4–5), which indicates that HpaII sites 4 and 5 are both unmethylated, was detectable in 50-day muscle DNA but diminished in older muscle. This process was accompanied by increasing intensity of a 9.5-kb fragment (HpaII 1–6), a result of progressive methylation at HpaII-sites 2–4 in the enhancer region (FIG. 12).

The present study on MyoD1 methylation patterns in rhabdomyosarcomas indicated that the degree of methylation in the MyoD1 immediate upstream region was different in adult and fetal muscle, and that embryonal rhabdomyosarcoma had a MyoD1 methylation pattern reminiscent of fetal muscle. In humans, the MyoD1 gene is expressed in fetal muscle but not in adult muscle. The progressive methylation at the 5' upstream region, therefore, may underlie the down-regulation of MyoD1 expression during skeletal muscle differentiation.

Table 1 summarizes the methylation status of the MyoD1 5' upstream region. The data clearly shows the utility of the present invention in diagnosing the different subtypes of rhabdomyosarcoma, and suggests that there are clinical applications for this methodology in stimulating myotube formation and subsequent myogenesis in patients in need of such treatment.

TABLE 1

Methylation status of the MyoD1 gene and RT-PCR analysis of Pax3/7-FKHR fusion genes

| Tumors | Spec No. | Diagnosis[a] | Methylation of MyoD1 5' region | Pax3/7-FKHR RT-PCR[b] |
|---|---|---|---|---|
| A1 | IRS 26 | Alv rms | unmethylated | + |
| A2 | IRS 42 | Alv rms | unmethylated | + |
| A3 | IRS 43 | Alv rms | unmethylated | NT |
| A4 | IRS 50 | Alv rms | unmethylated | + |
| A5 | IRS 65 | Alv rms | unmethylated | + |
| A6 | IRS 79 | Alv rms | unmethylated | – |
| A7 | IRS 81 | Alv rms | unmethylated | + |
| A8 | IRS 87 | Alv rms | partially methylated | – |
| A9 | IRS 92 | Alv rms | partially methylated | – |
| A10 | IRS 96 | Alv rms | unmethylated | NT |
| A11 | IRS 99 | Alv rms | unmethylated | + |
| A12 | IRS 126 | rms | unmethylated | + |
| A13 | S92-1586 | ? rms | unmethylated | +* |
| A14 | S92-1507 | Alv rms | unmethylated | NT |
| A15 | S92-15057 | Alv rms | unmethylated | NT |
| E1 | IRS 30 | Emb rms | partially methylated | NT |
| E2 | IRS 37 | Emb rms | partially methylated | NT |
| E3 | IRS 51 | Emb rms | partially methylated | – |

TABLE 1-continued

Methylation status of the MyoD1 gene and RT-PCR analysis of Pax3/7-FKHR fusion genes

| Tumors | Spec No. | Diagnosis[a] | Methylation of MyoD1 5' region | Pax3/7-FKHR RT-PCR[b] |
|---|---|---|---|---|
| E4 | IRS 59 | Emb rms | unmethylated** | – |
| E5 | IRS 75 | Emb rms | partially methylated | – |
| E6 | IRS 89 | rms | partially methylated | – |
| E7 | IRS 108 | Emb rms | partially methylated | – |
| E8 | IRS 159 | Emb rms | partially methylated | – |
| E9 | 590-1555 | Emb rms | partially methylated | – |
| E10 | S92-295 | Emb rms | partially methylate& | – |
| E11 | S92-1525 | B rms | partially methylated | – |

[a]: Alv: alveolar; rms: rhabdomyosarcoma; Emb: embryonal; B: botryoid.
[b]Simultaneous amplification of Pax3-FKHR and Pax7-FKHR using the Pax3/7 consensus primer. Subsequent PCR analysis using Pax3-specific or Pax7-specific primers indicated the presence of Pax7-FKHR in S92-1586 (*), and Pax3-FKHR in the rest of the translocation positive tumors.
NT: not tested.
**This tumor has a short deletion in the 5' flanking region of the MyoD1 gene.

The following references were cited herein:
American College of Medical Genetics Storage of Genetic Materials Committee 1995 Am. J. Hum. Genet, 57:1499–1500.
Barr F G 1993 Nature Genet., 3:113–117.
Bird A P 1996 Cancer Surveys, 28:87–101.
Braun E et al 1989 EMBO J., 8:701–709.
Casola S et al 1997 Oncogene, 14: 1503–1510.
Cheng P et al 1997 British Journal of Cancer, 75: 396–402.
Crescenzi M et al 1990 Proc. Natl. Acad. Sci., USA, 87:8442–8446.
Davis R J et al 1994 Cancer Res. 54: 2869–2872.
Davis R L et al 1990 Cell, 60:733–746.
Davis R L et al 1987 Cell, 51:987–1000.
Dias P et al 1992 Cancer Res., 52:6431–6439.
Dias P et al 1990 Am. J. Pathol., 137:1283–1291.
Enzinger F M and Weiss S W Soft tissue tumors. 3rd edition. St. Louis, Mo.: The CV Mosby Company, 1995: 539–577.
Epstein J A et al 1996 Proc. Natl. Acad. Sci., 93: 4213–4218.
Feil R et al 1994 Development, 120:2933–2943.
Feinberg et al 1995 J. Natl. Cancer Inst. Monographs, 17:21–26.
Friedman E Y and Rosbash M 1977 Nuc. Acids Res., 4:3455–3471.
Galili N et al 1993 Nat. Genet., 5: 230–235.
Hahnel R et al 1996 Anticancer Res., 16: 2111–2115.
Herman J G et al 1994 Proc. Natl. Acad. Sci., USA, 91: 9700–9704.
Iacopetta B J et al 1997 Anticancer Res., 17: 429–432.
Jones P A et al 1990 Proc. Natl. Acad. Sci., USA, 87:6117–6121.
Kinouchi Y et al 1996 Cancer Lett., 17: 105–108.
Konieczny S F and Emerson C P 1984 Cell, 38:791–800.
Leuschner I et al 1993 Am. J. Surg. Pathol., 17:221–230.
Li L and Olsen EN 1992 Adv. Cancer Res., 58:95–119.
Maroto M et al 1997 Cell, 89: 139–148.
Montarras D et al 1991 The New Biologist, 3:592–600.
Ng M H et al 1997 Blood, 89: 2500–2506.
Ogawa O et al 1993 Nature, 362: 749–751.
Ohlsson R et al 1993 Nature Genet., 4:94–97.
Ott M-O et al 1991 Development, 111:1097–1107.
Parham D M 1991 Cancer, 67:3072–3080.
Parham D M 1994 Sem Diag Pathol., 11:39–46.
Parham D M 1995 Adv. Pathol. Lab. Med., 8:223–245.
Pearson-White S H 1991 Nucleic Acids Res., 19:1148.
Reik W et al 1995 Hum. Mol. Genet., 4: 2379–2385.

Rhodes S J and Konieczny S F 1989 Genes Dev., 3:2050–2061.
Rideout W M et al 1994 Mol. Cell. Biol., 14:6143–6152.
Schroeder W T et al 1987 Am. J. Hum. Genet., 40:413–420.
Scrable H J 1989 Gene Chrom Cancer, 1:23–35.
Scrable H J 1990 Proc. Natl. Acad. Sci., USA, 87: 2182–2186.
Sorrentino V et al 1990 Nature, 345: 813–815.
Sotelo-Avila 1976 Perspect. Pediatr. Pathol., 3:255–272.
Southern E M 1975 J. Mol. Biol., 98:503–517.
Sublett J E et al 1995 Oncogene, 11: 545–552.
Tajbakhsh S et al 1997 Cell, 89: 127–138.
Taniguchi T 1997 Oncogene 14:1201–1206.
Taniguchi T 1995 Proc. Natl. Acad. Sci., USA, 92:2159–2163.
Tapscott S J et al 1993 Science, USA, 259:1450–1453.
Tornaletti S and Pfeifer G P 1995 Oncogene, 10:1493–1499.
Tsokos M et al 1985 Int'l Soc. Ped. Onc., XVIIth Mtg. Venice, Italy.
Weintraub H et al 1991 Science, USA, 251:761–766.
Wright W E et al 1989 Cell., 56:607–617.
Zhan S et al 1995 Oncogene, 11: 2503–2507.
Zhang P et al 1997 Nature 387: 151–158.
Zhang Y et al 1993 Am. J. Hum. Genet., 53:113–124.
Zingg J M et al 1991 Nuc. Acids Res., 19:6433–6439.

Any patents or publications mentioned in this specification are indicative of the levels of those skilled in the art to which the invention pertains. Further, these patents and publications are incorporated by reference herein to the same extent as if each individual publication was specifically and individually indicated to be incorporated by reference.

One skilled in the art will appreciate readily that the present invention is well adapted to carry out the objects and obtain the ends and advantages mentioned, as well as those objects, ends and advantages inherent herein. The present examples, along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. An isolated DNA molecule encoding a 5' upstream region from a human MyoD1 gene having a sequence shown in SEQ ID No. 1.

2. A vector comprising the DNA of claim 1.

3. A host cell transformed with the vector of claim 2.

4. An isolated DNA molecule fragment of the DNA of claim 1, wherein said fragment is selected from the group consisting of the sequences shown in SEQ ID No. 2, SEQ ID No. 3, SEQ ID No. 4 and SEQ ID No. 20.

5. A vector comprising the DNA of claim 4.

6. A host cell transformed with the vector of claim 5.

7. A method of determining the methylation pattern of a MyoD1 5' upstream region in tissues of an individual in need of such determination, comprising the steps of:

isolating genomic DNA from said tissues; and performing a methylation-sensitive PCR assay on said genomic DNA, wherein said methylation pattern is indicative of a neoplastic state of said tissues.

8. The method of claim 7, wherein said methylation-sensitive PCR assay comprises the steps of:

a) digesting said genomic DNA with a methylation-sensitive restriction enzyme to produce restricted DNA;

b) amplifying said restricted DNA using DNA oligonucleotides flanking a methylatable restriction site to produce amplified products;

c) analyzing said amplified products, wherein absence of an amplified product indicates hypomethylation, and wherein presence of an amplified product indicates hypermethylation.

9. The method of claim 7, wherein said tissue is selected from the group consisting of non-muscle cells, differentiated muscle tissue and myosarcomas.

10. The method of claim 7, wherein said individual is suspected of having a soft-tissue cancer.

11. The method of claim 10, wherein said soft-tissue cancer is rhabdomyosarcoma.

12. The method of claim 8, wherein hypermethylated DNA is indicative of alveolar rhabdomyosarcoma, wherein hypomethylated DNA is indicative of differentiated skeletal muscle tissue or normal non-muscle tissues, and wherein partially methylated DNA is indicative of embryonal rhabdomyosarcoma.

13. The method of claim 8, wherein said methylation-sensitive restriction enzyme is HhaI.

14. The method of claim 8, wherein said DNA oligonucleotides have the sequence shown in SEQ ID No. 7 and SEQ ID No. 8.

15. The method of claim 8, wherein the methylatable restriction site corresponds to the HhaI restriction enzyme consensus sequence shown in SEQ ID No. 18 and corresponding to position -839 of SEQ ID No. 1, wherein the internal cytosine residue may b e methylated.

16. A kit having reagents in which to perform a methylation-sensitive PCR assay to determine the methylation pattern of a MyoD1 5' upstream region.

17. The kit of claim 16, comprising reagents including buffers, DNA nucleotides and oligonucleotides, restriction enzymes, and conditions for optimal amplification.

18. A method of distinguishing differentiated skeletal muscle tissue, fetal muscle tissue and myosarcoma tissue by determining the methylation pattern of the 5' upstream region of the MyoD1 gene, comprising the steps of:
  a) isolating genomic DNA from said tissue;
  b) digesting said genomic DNA with at least one restriction enzyme to produce restricted DNA;
  c) analyzing said restricted DNA by Southern blot, wherein the DNA probes used for hybridization are selected from the group consisting of SEQ ID No. 2, SEQ ID No. 3, SEQ ID No. 4, and SEQ ID No. 20, wherein the digestion pattern is indicative of the extent of methylation of the 5' upstream region of the MyoD1 gene.

19. The method of claim 18, wherein the extent of methylation of the 5' upstream region of the MyoD1 gene is selected from the group consisting of hypermethylated DNA, hypomethylated DNA, and partially methylated DNA, wherein hypermethylated DNA is indicative of alveolar rhabdomyosarcoma, wherein hypomethylated DNA is indicative of differentiated skeletal muscle tissue or normal non-muscle tissues, and wherein partially methylated DNA is indicative of embryonal rhabdomyosarcoma.

20. The method of claim 18, wherein the restriction enzymes are selected from the group consisting of:
  a) PstI alone and PstI/HhaI double digestion;
  b) MspI alone and HpaII alone; and
  c) HhaI alone, HpaII alone, and HhaI/HpaII double digestion.

* * * * *

SEQUENCE LISTING

```
<160> NUMBER OF SEQ ID NOS:  20

<210> SEQ ID NO 1
<211> LENGTH: 2284
<212> TYPE: DNA
<213> ORGANISM: Homo sapiens
<220> FEATURE:
<221> NAME/KEY: promoter
<222> LOCATION: -1537..747
<223> OTHER INFORMATION: 5( upstream promoter region of the human MYOD1
      gene

<400> SEQUENCE: 1
aggaagaggc tgagagaccc ccatgggggt ggccggtatg ctgaggcttg tatgggagcc      60
agatatccca catcccatgg ggtggttgcc tcctcctgtt tccagccttt ccagtgaggc     120
tgcaggaaag agacacagct aaggcctgga gactcgtggc actccgtcag ggcatggtac     180
cacagatgag ttgtaagcct gcgggacaca gcatccaact ctgaaagccc cttgctcgaa     240
taaccctaca tcaccgcctg agggcttcca tatccttggt ctcttcagac tgtcatcccc     300
accacaatta ctccaagaaa ttactgtcat ccccaaatct ataactggaa actgaggctc     360
aggaaggaga catgacttcc acaaaatcac acagttggga aactctggag tctgcactca     420
actggtctgc aaaccgactc tcggagactt caggtgagat gaggtcaggt tctcaggcca     480
ggtcctgaag tttgacacct tggcgaaatg cactttcctt gactcagcac cgcagtgacg     540
gcggaacgaa gccccgagca gaagggcttt tcttcccagc tgaagaggca gctcagccta     600 gacccaggc atggcactgg acacccctgc tgtggaaacg tgcagattta gatggagggg      660
attcctaacc tgggcaggat ccgagtttgg agacattggc gcgaagttta gcagcaatct     720
ccgattcctg tacaaccata gctgggtttc taagcgtcta gggaagaagg actgggccca     780
cgacctgctg agcaactccc aggtcgggga ctggcggaat atcagagcct ctaccacccg     840
tttgtctcgg gctcgcccac ttcaactctc ggggtctctc cgcctgttgt tgcactcgtg     900
cgttctctgc ccctgacgct ctaagctttc tgctttctgc gtgtctctca gcctctttcg     960
gtccctcttt cacggtctca ctcctcagct ctgtgccccc aatgccttgc ctctctccaa    1020
```

-continued

```
atctctcact acctgatttc tacagccgct ctacccatgg gtcccccaca aatcaggggt      1080
acagaggagt attgaaagtc agctcagagg tgagcgcgcg cagccagcgt ttcccgcgga      1140
tacagcagtc gggtgttgga gaggtttgga aagggcgtgc cggagagcca agtgtcagcc      1200
gcctagggct tgccggtcgc tccctccctc cctgcccggt aggggaccta gcgcgcacgc      1260
cagtgtggag gggcgggctg gctggccagt ctcgggcccc tcggccaccc cggggacccc      1320
ccccaagccc cgcccccgag tgttcctatt ggcctcggac tcccctcc ccagctgccc        1380 gcctgggctc cggggcgttt aggctactac ggataaatag cccagggcgc ctggccgaga      1440
agctaggggt caggaagccc tggggcgctg ccgccgcttt ccttaaccac aaatcaggcc      1500
ggacaggaga gggaggggtg ggggacagtg ggtggggatt cagactgcca gcactttgct      1560
atctacagcc ggggctcccg agcggcagaa agttccggcc actctctgcc gcttgggttg      1620
ggcgaaagcc aggaccgtgc cgcgccaccg ccaggatatg gagctactgt cgccaccgct      1680
ccgcgacgta gacctgacgg cccccgacgg ctctctctgc tcctttgcca caacggacga      1740
cttctatgac gacccgtgtt tcgactcccc ggacctgcgc ttcttcgaag acctggaccc      1800
gcgcctgatg cacgtgggcg cgctcctgaa acccgaagag cactcgcact tccccgcggc      1860
ggtgcacccg gccccgggcg cacgtgagga cgagcatgtg cgcgcgccca gcgggcacca      1920
ccaggcgggc cgctgcctac tgtgggcctg caaggcgtgc aagcgcaaga ccaccaacgc      1980
cgaccgccgc aaggccgcca ccatgcgcga gcggcgccgc ctgagcaaag taaatgaggc      2040 cttttgagaca ctcaagcgct gcacgtcgag caatccaaac cagcggttgc ccaaggtgga    2100
gatcctgcgc aacgccatcc gctatatcga gggcctgcag gctctgctgc gcgaccagga     2160
cgccgcgccc cctggcgcag ccgccttcta tgcgccgggc ccgctgcccc cgggccgcgg     2220
cggcgagcac tacagcggcg actccgacgc gtccagcccg cgctccaact gctccgacgg     2280
catg                                                                  2284
```

<210> SEQ ID NO 2
<211> LENGTH: 2021
<212> TYPE: DNA
<213> ORGANISM: Homo sapiens
<220> FEATURE:
<223> OTHER INFORMATION: PstI fragment (PP2.0) used as a hybridization
      probe

<400> SEQUENCE: 2

```
ctgcaggaaa gagacacagc taaggcctgg agactcgtgg cactccgtca gggcatggta       60
ccacagatga gttgtaagcc tgcgggacac agcatccaac tctgaaagcc ccttgctcga      120
ataaccctac atcaccgcct gagggcttcc atatccttgg tctcttcaga ctgtcatccc      180
caccacaatt actccaagaa attactgtca tccccaaatc tataactgga aactgaggct      240
caggaaggag acatgacttc cacaaaatca cacagttggg aaactctgga gtctgcactc      300
aactggtctg caaaccgact ctcggagact tcaggtgaga tgaggtcagg ttctcaggcc      360
aggtcctgaa gtttgacacc ttggcgaaat gcactttcct tgactcagca ccgcagtgac      420
ggcggaacga agccccgagc agaagggctt ttcttcccag ctgaagaggc agctcagcct      480
agaccccagt catggcactg dacaccctg ctgtggaaac gtgcagattt agatggaggg       540
gattcctaac ctgggcagga tccgagtttg agagattgg cgcgaagttt agcagcaatc       600
tccgattcct gtacaaccat agctgggttt ctaagcgtct agggaagaag gactgggccc      660
acgacctgct gagcaactcc caggtcgggg actggcggaa tatcagagcc tctacgaccc     720
```

```
gtttgtctcg ggctcgccca cttcaactct cggggtctct ccgcctgttg ttgcactcgt    780
gcgttctctg ccctgacgc tctaagcttt ctgctttctg cgtgtctctc agcctctttc    840
ggtccctctt tcacggtctc actcctcagc tctgtgcccc caatgccttg cctctctcca    900
aatctctcac gacctgattt ctacagccgc tctacccatg ggtcccccac aaatcagggg    960
tacagaggag tattgaaagt cagctcagag gtgagcgcgc gcagccagcg tttcccgcgg   1020
atacagcagt cgggtgttgg agaggtttgg aaagggcgtg ccggagagcc aagtgtcagc   1080
cgcctagggc ttgccggtcg ctccctccct ccctgcccgg tagggaccct agcgcgcacg   1140
ccagtgtgga ggggcgggct ggctggccag tctcgggccc ctcggccacc ccggggaccc   1200
cccccaagcc ccgcccccga gtgttcctat tggcctcgga ctccccctcc cccagctgcc   1260
cgcctgggct ccggggcgtt taggctacta cggataaata gcccagggcg cctggccgag   1320
aagctagggg tgaggaagcc ctggggcgct gccgccgctt tccttaacca caaatcaggc   1380
cggacaggag agggaggggt gggggacagt gggtgtgggat tcagactgcc agcactttgc   1440
tatctacagc cggggctccc gagcggcaga aagttccggc cactctctgc cgcttgggtt   1500
gggcgaaagc caggaccgtg ccgcgccacc gccaggatat ggagctactg tcgccaccgc   1560
tccgcgacgt agacctgacg gccccgacg gctctctctg ctcctttgcc acaacggacg   1620
acttctatga cgacccgtgt ttcgactccc cggacctgcg cttcttcgaa gacctggacc   1680
cgcgcctgat gcacgtgggc gcgctcctga acccgaaga gcactcgcac ttccccgcgg   1740
cggtgcaccc ggccccgggc gcacgtgagg acgagcatgt gcgcgcgccc agcgggcacc   1800
accaggcggg ccgctgccta ctgtgggcct gcaaggcgtg caagcgcaag accaccaacg   1860
ccgaccgccg caaggccgcc accatgcgcg agcggcgccg cctgagcaaa gtaaatgagg   1920
cctttgagac actcaagcgc tgcacgtcga gcaatccaaa ccagcggttg cccaaggtgg   1980
agatcctgcg caacgccatc cgctatatcg agggcctgca g                      2021
```

<210> SEQ ID NO 3
<211> LENGTH: 563
<212> TYPE: DNA
<213> ORGANISM: Homo sapiens
<220> FEATURE:
<222> LOCATION: -1417..-861
<223> OTHER INFORMATION: PstI-BamHI fragment (PB0.5) used as a
     hybridization probe

<400> SEQUENCE: 3

```
ctgcaggaaa gagacacagc taaggcctgg agactcgtgg cactccgtca gggcatggta     60
ccacagatga gttgtaagcc tgcgggacac agcatccaac tctgaaagcc ccttgctcga    120
ataaccctac atcaccgcct gagggcttcc atatccttgg tctcttcaga ctgtcatccc    180
caccacaatt actccaagaa attactgtca tccccaaatc tataactgga aactgaggct    240
caggaaggag acatgacttc cacaaaatca cacagttggg aaactctgga gtctgcactc    300
aactggtctg caaaccgact ctcggagact tcaggtgaga tgaggtcagg ttctcaggcc    360
aggtcctgaa gtttgacacc ttggcgaaat gcactttcct tgactcagca ccgcagtgac    420
ggcggaacga agcccgagc agaagggctt ttcttcccag ctgaagaggc agctcagcct    480
agaccccagg catggcactg acacccctg ctgtggaaac gtgcagattt agatggaggg    540
gattcctaac ctgggcagga tcc                                            563
```

```
<210> SEQ ID NO 4
<211> LENGTH: 570
<212> TYPE: DNA
<213> ORGANISM: Homo sapiens
<220> FEATURE:
<222> LOCATION: -229..336
<223> OTHER INFORMATION: SmaI fragment (SS0.5) used as a hybridization
      probe

<400> SEQUENCE: 4
cccggggacc ccccccaagc cccgccccg  agtgttccta ttggcctcgg actccccctc    60
ccccagctgc cgcctgggc  tccggggcgt ttaggctact acgataaat  agcccagggc   120 gcctggccga gaagctaggg gtgaggaagc cctggggcgc tgccgccgct ttccttaacc   180
acaaatcagg ccggacagga gagggagggg tgggggacag tgggtgggga ttcagactgc   240
cagcactttg ctatctacag ccggggctcc cgagcggcag aaagttccgg ccactctctg   300
ccgcttgggt tgggcgaaag ccaggaccgt gccgcgccac cgccaggata tggagctact   360
gtcgccaccg ctccgcgacg tagacctgac ggcccccgac ggctctctct gctcctttgc   420
cacaacggac gacttctatg acgacccgtg tttcgactcc ccggacctgc gcttcttcga   480
agacctggac ccgcgcctga tgcacgtggg cgcgctcctg aaacccgaag agcactcgca   540
cttccccgcg gcggtgcacc cggccccggg                                    570

<210> SEQ ID NO 5
<211> LENGTH: 18
<212> TYPE: DNA
<213> ORGANISM: artificial sequence
<220> FEATURE:
<221> NAME/KEY: primer_bind
<223> OTHER INFORMATION: M1 primer used to amplify fragment
      corresponding to nucleotides 7-120 of the cDNA sequence of human
      MyoD1 gene

<400> SEQUENCE: 5
actgccagca ctttgcat                                                  18

<210> SEQ ID NO 6
<211> LENGTH: 20
<212> TYPE: DNA
<213> ORGANISM: artificial sequence
<220> FEATURE:
<221> NAME/KEY: primer_bind
<223> OTHER INFORMATION: M2 primer used to amplify fragment
      corresponding to nucleotides 7-120 of the cDNA sequence of human
      MyoD1 gene

<400> SEQUENCE: 6
atcctggcgg tggcgcggca                                                20

<210> SEQ ID NO 7
<211> LENGTH: 19
<212> TYPE: DNA
<213> ORGANISM: artificial sequence
<220> FEATURE:
<221> NAME/KEY: primer_bind
<223> OTHER INFORMATION: MetF primer used to amplify internal
      methylation sites

<400> SEQUENCE: 7
ccgagtttgg agagattgg                                                 19
```

```
<210> SEQ ID NO 8
<211> LENGTH: 19
<212> TYPE: DNA
<213> ORGANISM: artificial sequence
<220> FEATURE:
<221> NAME/KEY: primer_bind
<223> OTHER INFORMATION: MetF primer used to amplify internal
      methylation sites

<400> SEQUENCE: 8
gaccccgaga gttgaagtg                                                  19

<210> SEQ ID NO 9
<211> LENGTH: 19
<212> TYPE: DNA
<213> ORGANISM: artificial sequence
<220> FEATURE:
<221> NAME/KEY: primer_bind
<223> OTHER INFORMATION: MyoD1 primer M15 used to amplify MyoD1 cDNA
      synthesized via AMV reverse transcriptase

<400> SEQUENCE: 9
gcggcggaac tgctgcgaa                                                  19

<210> SEQ ID NO 10
<211> LENGTH: 19
<212> TYPE: DNA
<213> ORGANISM: artificial sequence
<220> FEATURE:
<221> NAME/KEY: primer_bind
<223> OTHER INFORMATION: MyoD1 primer M16 used to amplify MyoD1 cDNA
      synthesized via AMV reverse transcriptase

<400> SEQUENCE: 10
gatgcgctcc acgatgctg                                                  19

<210> SEQ ID NO 11
<211> LENGTH: 18
<212> TYPE: DNA
<213> ORGANISM: artificial sequence
<220> FEATURE:
<221> NAME/KEY: primer_bind
<223> OTHER INFORMATION: (-actin primer ACTF used to amplify (-actin
      product

<400> SEQUENCE: 11
actcttccag ccttcctt                                                   18

<210> SEQ ID NO 12
<211> LENGTH: 18
<212> TYPE: DNA
<213> ORGANISM: artificial sequence
<220> FEATURE:
<221> NAME/KEY: primer_bind
<223> OTHER INFORMATION: (-actin primer ACTF used to amplify (-actin
      product

<400> SEQUENCE: 12
ctccttctgc atcctgtc                                                   18

<210> SEQ ID NO 13
<211> LENGTH: 20
<212> TYPE: DNA
<213> ORGANISM: artificial sequence
<220> FEATURE:
<221> NAME/KEY: primer_bind
<223> OTHER INFORMATION: FKHR reverse primer used to amplify a 219 bp
      fragment for Pax3-FKHR and a 206 bp fragment for Pax7-FKHR
```

```
<400> SEQUENCE: 13
attgagcatc caccaagaac                                                  20

<210> SEQ ID NO 14
<211> LENGTH: 18
<212> TYPE: DNA
<213> ORGANISM: artificial sequence
<220> FEATURE:
<221> NAME/KEY: primer_bind
<223> OTHER INFORMATION: PAX3/7 consensus primer used to amplify a 219
      bp fragment for Pax3-FKHR and a 206 bp fragment for Pax7-FKHR

<400> SEQUENCE: 14
gacagcagct ctgcctac                                                    18

<210> SEQ ID NO 15
<211> LENGTH: 20
<212> TYPE: DNA
<213> ORGANISM: artificial sequence
<220> FEATURE:
<221> NAME/KEY: primer_bind
<223> OTHER INFORMATION: FKHR forward primer used to amplify the normal
      FKHR transcript

<400> SEQUENCE: 15
ggtcaagagc gtgccctact                                                  20

<210> SEQ ID NO 16
<211> LENGTH: 18
<212> TYPE: DNA
<213> ORGANISM: artificial sequence
<220> FEATURE:
<221> NAME/KEY: primer_bind
<223> OTHER INFORMATION: Pax3-specific primer used to amplify the Pax3
      gene

<400> SEQUENCE: 16
actgcctccc cagcacca                                                    18

<210> SEQ ID NO 17
<211> LENGTH: 18
<212> TYPE: DNA
<213> ORGANISM: artificial sequence
<220> FEATURE:
<221> NAME/KEY: primer_bind
<223> OTHER INFORMATION: Pax7-specific primer used to amplify the Pax7
      gene

<400> SEQUENCE: 17
ttctccagct actctgac                                                    18

<210> SEQ ID NO 18
<211> LENGTH: 4
<212> TYPE: DNA
<213> ORGANISM: Homo sapiens
<220> FEATURE:
<223> OTHER INFORMATION: HhaI restriction enzyme consensus sequence

<400> SEQUENCE: 18 gcgc                                                                    4

<210> SEQ ID NO 19
<211> LENGTH: 4
<212> TYPE: DNA
<213> ORGANISM: Homo sapiens
<220> FEATURE:
<223> OTHER INFORMATION: HpaII restriction enzyme consensus sequence
```

```
<400> SEQUENCE: 19 ccgg                                                                           4

<210> SEQ ID NO 20
<211> LENGTH: 1312
<212> TYPE: DNA
<213> ORGANISM: Homo sapiens
<220> FEATURE:
<223> OTHER INFORMATION: PstI-EheI fragment (PE1.3) inserted in the
      multiple cloning region of a pGLe enhancer vector to construct
      the transfection plasmid

<400> SEQUENCE: 20
ctgcaggaaa gagacacagc taaggcctgg agactcgtgg cactccgtca gggcatggta        60
ccacagatga gttgtaagcc tgcgggacac agcatccaac tctgaaagcc ccttgctcga       120
ataaccctac atcaccgcct gagggcttcc atatccttgg tctcttcaga ctgtcatccc       180
caccacaatt actccaagaa attactgtca tccccaaatc tataactgga aactgaggct       240
caggaaggag acatgacttc cacaaaatca cacagttggg aaactctgga gtctgcactc       300
aactggtctg caaaccgact ctcggagact tcaggtgaga tgaggtcagg ttctcaggcc       360
aggtcctgaa gtttgacacc ttggcgaaat gcactttcct tgactcagca ccgcagtgac       420
ggcggaacga agccccgagc agaagggctt ttcttcccag ctgaagaggc agctcagcct       480 agacccagg catggcactg gacacccctg ctgtggaaac gtgcagattt agatggaggg        540
gattcctaac ctgggcagga tccgagtttg gagagattgc cgcgaagttt agcagcaatc       600
tccgattcct gtacaaccat agctgggttt ctaagcgtct agggaagaag gactgggccc       660
acgacctgct gagcaactcc caggtcgggg actggcggaa tatcagagcc tctacgaccc       720
gtttgtctcg ggctcgccca cttcaactct cggggtctct ccgcctgttg ttgcactcgt       780
gcgttctctg cccctgacgc tctaagcttt ctgctttctg cgtgtctctc agcctctttc       840
ggtccctctt tcacggtctc actcctcagc tctgtgcccc caatgccttg cctctctcca       900
aatctctcac gacctgattt ctacagccgc tctacccatg ggtccccac aaatcagggg       960 tacagaggag tattgaaagt cagctcagag gtgagcgcgc gcagccagcg tttcccgcgg      1020
atacagcagt cgggtgttgg agaggtttgg aaagggcgtg ccggagagcc aagtgtcagc      1080
cgcctagggc ttgccggtcg ctccctccct ccctgcccgg tagggaccct agcgcgcacg      1140
ccagtgtgga ggggcgggct ggctggccag tctcgggccc ctcggccacc ccggggaccc      1200 ccccaagcc ccgcccccga gtgttcctat tggcctcgga ctcccctcc cccagctgcc        1260 cgcctgggct ccggggcgtt taggctacta cggataaata gcccagggcg cc             1312
```